US012557968B2

(12) United States Patent
Meguro

(10) Patent No.: US 12,557,968 B2
(45) Date of Patent: Feb. 24, 2026

(54) MEDICAL IMAGE PROCESSING APPARATUS, ENDOSCOPE SYSTEM, DIAGNOSIS ASSISTANCE METHOD, AND PROGRAM

(71) Applicant: FUJIFILM Corporation, Tokyo (JP)

(72) Inventor: Misaki Meguro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 508 days.

(21) Appl. No.: 17/845,442

(22) Filed: Jun. 21, 2022

(65) Prior Publication Data

US 2022/0313067 A1 Oct. 6, 2022

Related U.S. Application Data

(63) Continuation of application No. PCT/JP2021/000327, filed on Jan. 7, 2021.

(30) Foreign Application Priority Data

Jan. 17, 2020 (JP) ................................. 2020-005765

(51) Int. Cl.
*A61B 1/00* (2006.01)
*G06T 7/00* (2017.01)
(52) U.S. Cl.
CPC .... *A61B 1/000095* (2022.02); *A61B 1/00006* (2013.01); *A61B 1/000096* (2022.02);
(Continued)
(58) Field of Classification Search
CPC ........ A61B 1/000095; A61B 1/000096; A61B 1/00006; A61B 1/00039; A61B 1/00045;
(Continued)

(56) References Cited

U.S. PATENT DOCUMENTS 10,531,815 B2 * 1/2020 Lu ............................ G06T 7/162
2004/0225223 A1 11/2004 Honda et al.
(Continued)

FOREIGN PATENT DOCUMENTS

CN 1777390 A 5/2006
CN 103649996 A 3/2014
(Continued)

OTHER PUBLICATIONS

International Preliminary Report On Patentability and Written Opinion issued in PCT/JP2021/000327 filed; issued Jul. 19, 2022.
(Continued)

*Primary Examiner* — Michael R Neff
(74) *Attorney, Agent, or Firm* — Studebaker Brackett PLLC

(57) ABSTRACT

There are provided a medical image processing apparatus, an endoscope system, a diagnosis assistance method, and a program capable of coping with an erroneous determination while utilizing an observation completion determination in which image processing is used and of suppressing oversight of an observation target part by a doctor. The medical image processing apparatus includes at least one processor. The at least one processor acquires a medical image; makes, on the basis of the medical image, an observation completion determination as to whether observation is completed for a target part; performs display control for causing a determined result of the observation completion determination to be displayed on a display device, receives a user input including an instruction for correcting display content indicating the determined result of the observation completion determination, and causes corrected content based on the user input to be reflected in the display.

27 Claims, 13 Drawing Sheets

(52) U.S. Cl.
    CPC ...... *A61B 1/00039* (2013.01); *A61B 1/00045* (2013.01); *G06T 7/0012* (2013.01); *G06T 2207/10068* (2013.01); *G06T 2207/20084* (2013.01); *G06T 2207/20092* (2013.01)

(58) Field of Classification Search
    CPC ......... G06T 7/0012; G06T 2207/10068; G06T 2207/20084; G06T 2207/20092
    USPC ....................................................... 382/128
    See application file for complete search history.

(56) References Cited

U.S. PATENT DOCUMENTS

| | | |
|---|---|---|
| 2014/0081129 A1 | 3/2014 | Lu et al. |
| 2017/0112578 A1 | 4/2017 | Ikuma et al. |
| 2018/0084970 A1 | 3/2018 | Harada et al. |
| 2019/0043215 A1* | 2/2019 | Ito ........................... A61B 34/20 |
| 2019/0374088 A1 | 12/2019 | Watanabe |
| 2020/0143936 A1* | 5/2020 | Kamon .................. G16H 30/40 |
| 2020/0320702 A1 | 10/2020 | Kamon |

FOREIGN PATENT DOCUMENTS

| | | |
|---|---|---|
| CN | 110008995 A | 7/2019 |
| CN | 110325100 A | 10/2019 |
| EP | 3 590 413 A1 | 1/2020 |
| JP | 2012-174222 A | 9/2012 |
| JP | 2016-002206 A | 1/2016 |
| JP | 6284439 B2 | 2/2018 |
| JP | 2018-050890 A | 4/2018 |
| JP | 2018-139848 A | 9/2018 |
| WO | 2016/009701 A1 | 1/2016 |
| WO | 2019/008941 A1 | 1/2019 |
| WO | 2019/138773 A1 | 7/2019 |

OTHER PUBLICATIONS

International Search Report issued in PCT/JP2021/000327; mailed Feb. 22, 2021.

The extended European search report issued by the European Patent Office on Jun. 9, 2023, which corresponds to European Patent Application No. 21741150.3-1126 and is related to U.S. Appl. No. 17/845,442.

An Office Action mailed by China National Intellectual Property Administration on Feb. 18, 2025, which corresponds to Chinese Patent Application No. 202180008430.6 and is related to U.S. Appl. No. 17/845,442; with English language translation.

An Office Action mailed by China National Intellectual Property Administration on Jul. 31, 2025, which corresponds to Chinese Patent Application No. 20210008430.6 and is related to U.S. Appl. No. 17/845,442; with English language translation.

\* cited by examiner

FIG. 10

<BEFORE CORRECTION>

<AFTER CORRECTION>

Observation of antrum is completed

FIG. 11

<BEFORE CORRECTION>

<AFTER CORRECTION>

MEDICAL IMAGE PROCESSING APPARATUS, ENDOSCOPE SYSTEM, DIAGNOSIS ASSISTANCE METHOD, AND PROGRAM

CROSS-REFERENCE TO RELATED APPLICATIONS

The present application is a Continuation of PCT International Application No. PCT/JP2021/000327 filed on Jan. 7, 2021 claiming priority under 35 U.S.C § 119(a) to Japanese Patent Application No. 2020-005765 filed on Jan. 17, 2020. Each of the above applications is hereby expressly incorporated by reference, in its entirety, into the present application.

BACKGROUND OF THE INVENTION

1. Field of the Invention

The present invention relates to a medical image processing apparatus, an endoscope system, a diagnosis assistance method, and a program.

2. Description of the Related Art

In an endoscopic examination, thorough observation of a plurality of parts of an examination target organ or the like is desired. In JP2018-50890A, there has been proposed an assistance technique for suppressing omission in imaging in the case where parts required to be imaged are determined in an examination target organ. An image display device described in JP2018-50890A detects a predetermined anatomic landmark from an endoscopic image, generates a map image representing an imaged region and a yet-to-be-imaged region in an examination target organ, and causes the map image to be displayed on a monitor.

JP2012-174222A describes an image recognition technique that uses machine learning. An image recognition apparatus described in JP2012-174222A performs a class recognition process on input image data and causes the class recognition result to be displayed on a display device. The image recognition apparatus described in JP2012-174222A receives a user's evaluation on the class recognition result, and performs additional training of an identification unit by using the user's evaluation result and the input image data as learning data so as to improve the recognition accuracy. According to paragraph 0057 of JP2012-174222A, the image recognition apparatus is installed in an endoscope control unit.

SUMMARY OF THE INVENTION

In an examination using a medical instrument such as an endoscope, the entirety of a target part needs to be thoroughly checked in accordance with the purpose of the examination. For example, when an internal part of the stomach is minutely divided, the internal part is constituted by ten or more sub-parts. Thus, a doctor may overlook a portion of the part when observing the inside of the stomach. In the field of medical images, development of a technique for performing various kinds of assistance by utilizing artificial intelligence (AI) is in progress. Such a technique automatically determines whether a doctor has completed observation of a specific part by utilizing the image recognition technology on medical images such as endoscopic images, and displays the determined result. Thus, the technique expectedly suppresses omission (oversight) in the observation.

However, a criterion of the determination regarding completion of the observation of a part made by the AI that uses deep learning or the like for suppressing oversight of a part to be observed may be different from a criterion of the determination regarding completion of the observation made by a doctor. The determination as to whether observation is completed for a certain part includes a subjective factor of a doctor himself/herself such as whether the doctor has deliberately performed the observation. Thus, it may be difficult to make such a determination with an ordinary image classification task based on image analysis as described in JP2012-174222A. Even though the AI determines that observation is completed for a certain part, there may be a case where the doctor has not actually performed the observation or a degree of the observation is insufficient. Thus, a discrepancy (disagreement) may occur between the observation completion determination made by the AI and the determination made by a person.

These issues described above are not specific to endoscopic examinations but are common issues expected in the case where a process of determining whether observation of a certain part is completed is performed for various medical images.

The present invention is made in view of such a circumstance, and an object thereof is to provide a medical image processing apparatus, an endoscope system, a diagnosis assistance method, and a program capable of overcoming at least one issue among the plurality of issues described above, of coping with an erroneous determination while utilizing an observation completion determination in which image processing is used, and of suppressing oversight of an observation target part by a doctor.

A medical image processing apparatus according to one aspect of the present disclosure is a medical image processing apparatus including at least one processor configured to acquire a medical image; make, on the basis of the medical image, an observation completion determination as to whether observation is completed for a target part; perform display control for causing a determined result of the observation completion determination to be displayed on a display device; receive a user input including an instruction for correcting display content indicating the determined result of the observation completion determination; and cause corrected content based on the user input to be reflected in the display.

According to the medical image processing apparatus of this aspect, the determined result of the observation completion determination for the part, which is obtained as a result of processing the medical image, is displayed on the display device. The user can perform a user input for correcting a display of the determined result. The content of the instructed correction based on the user input is reflected in the display on the display device, and the display for reporting completion or incompletion of the observation of the part is changed.

The expression "causing corrected content to be reflected in a display" may be understood as displaying the corrected content, that is, displaying the corrected content in which the correction is reflected.

In the medical image processing apparatus according to this aspect, in the case where an observation completion determination obtained for a part as a result of the at least one processor processing the medical image differs from a determination made by a doctor (user), a display of the determined result can be corrected in accordance with the user input in response to an interaction of the user. Thus, correct information regarding the observation completed part can be displayed, and assistance for suppressing oversight of a part can be provided.

The medical image processing apparatus may be constituted by a single apparatus or may be constituted by a combination of a plurality of apparatuses. For example, the medical image processing apparatus may be implemented by using one or a plurality of computers. The term "apparatus" includes concepts of "system" and "module".

The medical image processing apparatus according to another aspect of the present disclosure may further include the display device configured to display the determined result of the observation completion determination.

In the medical image processing apparatus according to another aspect of the present disclosure, the at least one processor may be configured to determine that the observation is completed for a specific part in a case where a mark for the specific part is present in the medical image.

The "mark" refers to a landmark. The "mark" may be a characteristic shape and/or pattern of the part, or may include a non-human-body component, such as a portion of an endoscope, that is in an image together with the specific part.

The "specific part" may be a portion, that is, a sub-part, of an examination target organ or may be the entire organ. In the case where a plurality of parts are thoroughly observed, each of the plurality of parts can be set as the "specific part".

In the medical image processing apparatus according to another aspect of the present disclosure, the at least one processor may be configured to determine that the observation is completed for a specific part in a case where the specific part is present in the medical image for a predetermined period or longer.

For example, in time-series medical images such as a moving image, in the case where the same part is present in the images for a predetermined period, it can be inferred that the doctor has deliberately observed the specific part. The "predetermined period" used herein refers to a predetermined length of time.

In the medical image processing apparatus according to another aspect of the present disclosure, the at least one processor may be configured to determine that the observation is completed for a specific part in a case where a mark for the specific part is present in a central portion of the medical image.

The term "central portion" is not limited to the exact center but includes a range that is understood as an approximately central portion in an image region of the medical image. It is considered that a target is often kept in the central portion of the image when a doctor deliberately observes a specific part while paying attention to the part.

In the medical image processing apparatus according to another aspect of the present disclosure, when a first condition is that a mark for a specific part is present in the medical image, a second condition is that the specific part is present in the medical image for a predetermined period or longer, and a third condition is that the mark for the specific part is present in a central portion of the medical image, the at least one processor is configured to determine that the observation is completed for the specific part in a case where at least one condition of the first condition, the second condition, or the third condition is met.

The at least one processor may determine that the observation is completed in the case where any one condition among the first condition, the second condition, and the third condition is met, or may determine that the observation is completed when two or more conditions are met.

In the medical image processing apparatus according to another aspect of the present disclosure, the at least one processor may be configured to receive an input of an image-capturing instruction signal indicating an image-capturing timing of a still image, and determine, in a case of receiving an input of the image-capturing instruction signal, that the observation is completed for a part of which the still image is captured.

The medical image processing apparatus according to another aspect of the present disclosure may further include a memory, in which the memory is configured to store the medical image and determined result information indicating the determined result of the observation completion determination, and in a case where the at least one processor receives the user input, user input information, the determined result information that is a target to be corrected based on the user input, and the medical image from which the determined result information is obtained are stored in the memory in association with one another.

According to this aspect, the medical image from which the at least one processor has made an erroneous observation completion determination and information on a correct determined result for the medical image are stored in the memory. By utilizing, as learning data, this data stored in the memory, additional training and/or development of a new model for improving the inference accuracy of an inference model used in the observation completion determination process can be performed.

The medical image processing apparatus according to another aspect of the present disclosure may further include a memory, and a communication apparatus, in which the memory is configured to store the medical image and determined result information indicating the determined result of the observation completion determination, and the communication apparatus is configured to, in a case where the at least one processor receives the user input, transmit user input information, the determined result information that is a target to be corrected based on the user input, and the medical image from which the determined result information is obtained, to an external device.

According to this aspect, the medical image from which the at least one processor has made an erroneous observation completion determination and information on a correct determined result for the medical image are transmitted to the external device. The data transmitted to the external device can be utilized as learning data, and the external device or another device other than the external device can perform additional training and/or development of a new model for improving the inference accuracy of an inference model used in the observation completion determination process.

In the medical image processing apparatus according to another aspect of the present disclosure, the at least one processor may be configured to receive the user input for correcting an observation incomplete display for a part for which the determined result of the observation completion determination indicates that the observation is incomplete, to an observation completed display indicating that the observation is completed, and change, on the basis of the user input, display content of the observation incomplete display to display content of the observation completed display.

In the medical image processing apparatus according to another aspect of the present disclosure, the at least one processor may be configured to receive the user input for correcting an observation completed display for a part for which the determined result of the observation completion determination indicates that the observation is completed, to an observation incomplete display indicating that the observation is incomplete, and change, on the basis of the user input, display content of the observation completed display to display content of the observation incomplete display.

In the medical image processing apparatus according to another aspect of the present disclosure, the at least one processor may be configured to receive the user input for correcting a display of part information on an observation completed part for which it is determined that the observation is completed in the observation completion determination, to a display of part information indicating another part, and correct, on the basis of the user input, display content of the part information on the observation completed part.

In the medical image processing apparatus according to another aspect of the present disclosure, the at least one processor may be configured to cause the medical image to be displayed in a first display region of the display device, and cause the determined result of the observation completion determination to be displayed in a second display region of the display device, the second display region being different from the first display region.

In the medical image processing apparatus according to another aspect of the present disclosure, the at least one processor may be configured to cause part information on an observation completed part to be displayed using a model figure that schematically represents a part of a human body including the target part.

The model figure may be, for example, a schematic image that models the shape of an organ.

In the medical image processing apparatus according to another aspect of the present disclosure, the at least one processor may be configured to cause an observation completed part and an observation incomplete part to be displayed in different colors in the model figure.

According to such an aspect, the doctor can easily grasp the observation completed part and the observation incomplete part at a glance.

In the medical image processing apparatus according to another aspect of the present disclosure, the at least one processor may be configured to cause part information on an observation completed part to be displayed as text information.

The medical image processing apparatus according to another aspect of the present disclosure may further include an input device to be used by a user to input the instruction, in which the at least one processor is configured to receive the user input from the input device.

The input device may include at least one of a keyboard, a touch panel, a voice input device, a switch provided in an endoscope, or a foot switch.

In the medical image processing apparatus according to another aspect of the present disclosure, the at least one processor may be configured to set a plurality of parts that are observation targets, make the observation completion determination for each part of the plurality of parts, and cause, on the basis of determined results of the observation completion determinations, information indicating an observation completed part among the plurality of parts and information indicating an observation incomplete part among the plurality of parts to be displayed.

According to such an aspect, information on a part for which observation is completed (observation completed part) and information on a part for which observation is incomplete (observation incomplete part) can be displayed by explicitly distinguishing between these parts. Thus, in the case where thorough observation of a plurality of parts is desired, omission (oversight of a part) in observation can be effectively suppressed.

In the medical image processing apparatus according to another aspect of the present disclosure, the at least one processor may be configured to make the observation completion determination by using a neural network.

The at least one processor can perform the observation completion determination by using a trained model trained through machine learning such as deep learning so as to perform a part recognition task and an observation completion determination task.

In the medical image processing apparatus according to another aspect of the present disclosure, the at least one processor may be configured to acquire the medical images that are in time series.

The time-series medical images may be a moving image or may be a group of images captured at specific time intervals as in continuous image-capturing or interval image-capturing. In addition, the time intervals in time-series image-capturing need not necessarily be constant.

The medical image may be an endoscopic image captured with an endoscope. The endoscope may be an endoscopescope or a capsule endoscope.

An endoscope system according to another aspect of the present disclosure is an endoscope system including an endoscope, and at least one processor, in which the at least one processor is configured to acquire an endoscopic image obtained by imaging inside of a body by using the endoscope; make, on the basis of the endoscopic image, an observation completion determination as to whether observation is completed for a target part; perform display control for causing a determined result of the observation completion determination to be displayed on a display device; receive a user input including an instruction for correcting display content indicating the determined result of the observation completion determination; and cause corrected content based on the user input to be reflected in the display.

According to the endoscope system of this aspect, the determined result of the observation completion determination can be displayed in real time in the endoscopic image that is being observed. In the case where an erroneously determined result is displayed, the user can timely correct the display to correct display content.

A diagnosis assistance method according to another aspect of the present disclosure is a diagnosis assistance method implemented by at least one processor, including, with the at least one processor, acquiring a medical image; making, on the basis of the medical image, an observation completion determination as to whether observation is completed for a target part; performing display control for causing a determined result of the observation completion determination to be displayed on a display device; receiving a user input including an instruction for correcting display content indicating the determined result of the observation completion determination; and causing corrected content based on the user input to be reflected in the display.

A program according to another aspect of the present disclosure is a program for causing a computer to implement a function of acquiring a medical image; a function of making, on the basis of the medical image, an observation completion determination as to whether observation is completed for a target part; a function of performing display control for causing a determined result of the observation completion determination to be displayed on a display device; a function of receiving a user input including an instruction for correcting display content indicating the determined result of the observation completion determination; and a function of causing corrected content based on the user input to be reflected in the display.

According to the present invention, whether observation is completed for a target part can be determined on the basis of image processing of a medical image, and the determined result can be displayed. In the case where the determined result is erroneous, the display can be corrected to correct display content on the basis of a user input. Thus, oversight of a part can be suppressed, and assistance may be provided so that an appropriate examination is performed.

BRIEF DESCRIPTION OF THE DRAWINGS

FIG. 10 is an example of the displayed image in the case where a display of the observation incompletion information based on the determined result of the observation completion determination is corrected to the observation completion information;

FIG. 11 is an example of the displayed image in the case where a display of the observation completion information for a part based on the determined result of the observation completion determination is corrected to the observation completion information for another part;

DESCRIPTION OF THE PREFERRED EMBODIMENTS

Preferred embodiments of the present invention will be described in detail below with reference to the accompanying drawings. The same constituent elements are denoted by the same reference signs herein, and redundant description will be appropriately omitted.

Overview of Endoscope System

Figure 1:
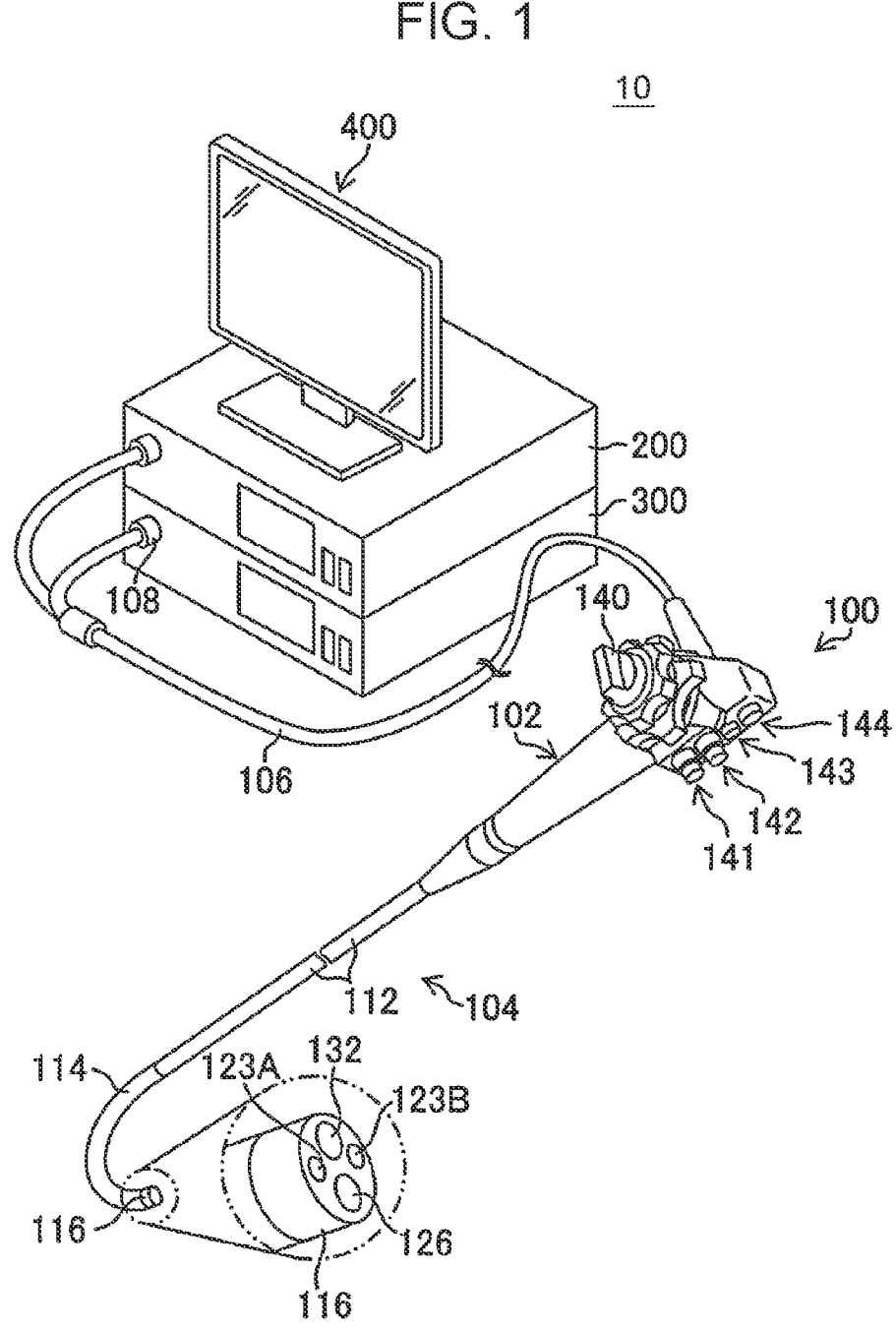
FIG. 1 is a perspective view illustrating, as an example, an external appearance of an endoscope system according to an embodiment of the present invention.

FIG. 1 is a perspective view illustrating, as an example, an external appearance of an endoscope system 10 according to an embodiment of the present invention. The endoscope system 10 includes an endoscope 100, a processor device 200, a light source device 300, and a monitor 400.

The endoscope 100 is an electronic endoscope and is, for example, a flexible endoscope. The endoscope 100 includes a handheld operation section 102, an insertion section 104, and a universal cable 106. The handheld operation section 102 includes an angle knob 140, an air/water supply button 141, a suction button 142, a function button 143, and an image-capturing button 144.

The angle knob 140 is used for a bending operation for instructing a bending direction and a bending amount of a bending part 114 of the insertion section 104. The angle knob 140 includes two types of knobs, that is, an up-down angle knob for bending the bending part 114 in an up-down direction and a left-right angle knob for bending the bending part 114 in a left-right direction.

The air/water supply button 141 receives an air supply instruction operation and a water supply instruction operation. The suction button 142 receives a suction instruction operation. The function button 143 is assigned various functions. The function button 143 receives instruction operations for the various functions. The image-capturing button 144 receives image-capturing instruction operations. The term "image-capturing" includes both concepts of capturing of a still image and capturing of a moving image. The image-capturing instruction operations include an operation of giving an instruction on an image-capturing timing of a still image, an operation of giving an instruction on an image-capturing start timing of a moving image, and an operation of giving an instruction on an image-capturing end timing of the moving image.

A user grips the handheld operation section 102 and operates the endoscope 100 so as to insert the insertion section 104 into the body of a subject. In this manner, the user observes the inside of the body. The "user" used herein refers to a doctor who is an operator. The term "subject" is synonymous with a patient, a test subject, or a person subjected to an examination.

The insertion section 104 is a portion to be inserted into the body of the subject. The insertion section 104 is coupled to the handheld operation section 102. The insertion section 104 includes a soft part 112, the bending part 114, and a tip rigid part 116 sequentially from the handheld operation section 102 side.

The soft part 112 is a portion that has flexibility and is provided between the handheld operation section 102 and the bending part 114. The bending part 114 is a portion including a mechanism that is bendable in response to an operation on the handheld operation section 102. By operating the angle knob 140, the user can bend the bending part 114 so as to change the direction of the tip rigid part 116 upward, downward, leftward, or rightward.

FIG. 1 illustrates a portion of the tip rigid part 116 in an enlarged manner. The tip rigid part 116 is provided with an imaging unit including an imaging lens 132, an illumination unit including illumination lenses 123A and 123B, and a forceps port 126. The imaging unit is illustrated with a reference sign 130 in FIG. 2. The illumination unit is illustrated with a reference sign 123 in FIG. 2.

At the time of observation and treatment, white light and/or narrow-range light can be radiated through the illumination lenses 123A and 123B in response to an operation performed by the user. The narrow-range light includes at least one of red narrow-range light, green narrow-range light, blue narrow-range light, or violet narrow-range light.

When the air/water supply button 141 is operated, wash water is ejected from a water supply nozzle (not illustrated) or a gas is ejected from an air supply nozzle (not illustrated). The wash water and the gas can be used for cleaning the imaging lens 132, the illumination lenses 123A and 123B, and so on. Note that the water supply nozzle and the air supply nozzle may be integrated.

The forceps port 126 communicates with a treatment tool insertion path (not illustrated) that is disposed inside the insertion section 104. A treatment tool (not illustrated) is inserted in the treatment tool insertion path. The handheld operation section 102 is provided with a treatment tool introduction port (not illustrated) through which a treatment tool is inserted into the treatment tool insertion path. Examples of the treatment tool include biopsy forceps, a catheter, a high-frequency snare, and the like. The examples of the treatment tool also include a guide tube, a trocar tube, a sliding tube, and the like. The treatment tool is supported in the treatment tool insertion path such that the treatment tool can be appropriately moved forward and backward. At the time of removal of a tumor or the like, the user can perform necessary treatment on a subject by using the treatment tool.

The universal cable 106 is a cable for connecting the endoscope 100 to the processor device 200 and the light source device 300. An electric cable and a light guide that extend from the insertion section 104 are inserted in the universal cable 106. The electric cable includes a communication cable for use in signal transmission and a power supply cable for use in power supply. The endoscope 100 is connected to the processor device 200 and the light source device 300 through the universal cable 106.

Note that in addition to the handheld operation section 102, the endoscope system 10 may include a foot switch (not illustrated) and/or a voice input device (not illustrated), as an input device (or input devices) for receiving an instruction or the like input from the user. The foot switch includes a pedal and a cable. The cable of the foot switch is connected to the processor device 200.

Example of Configuration of Endoscope System

Figure 2:
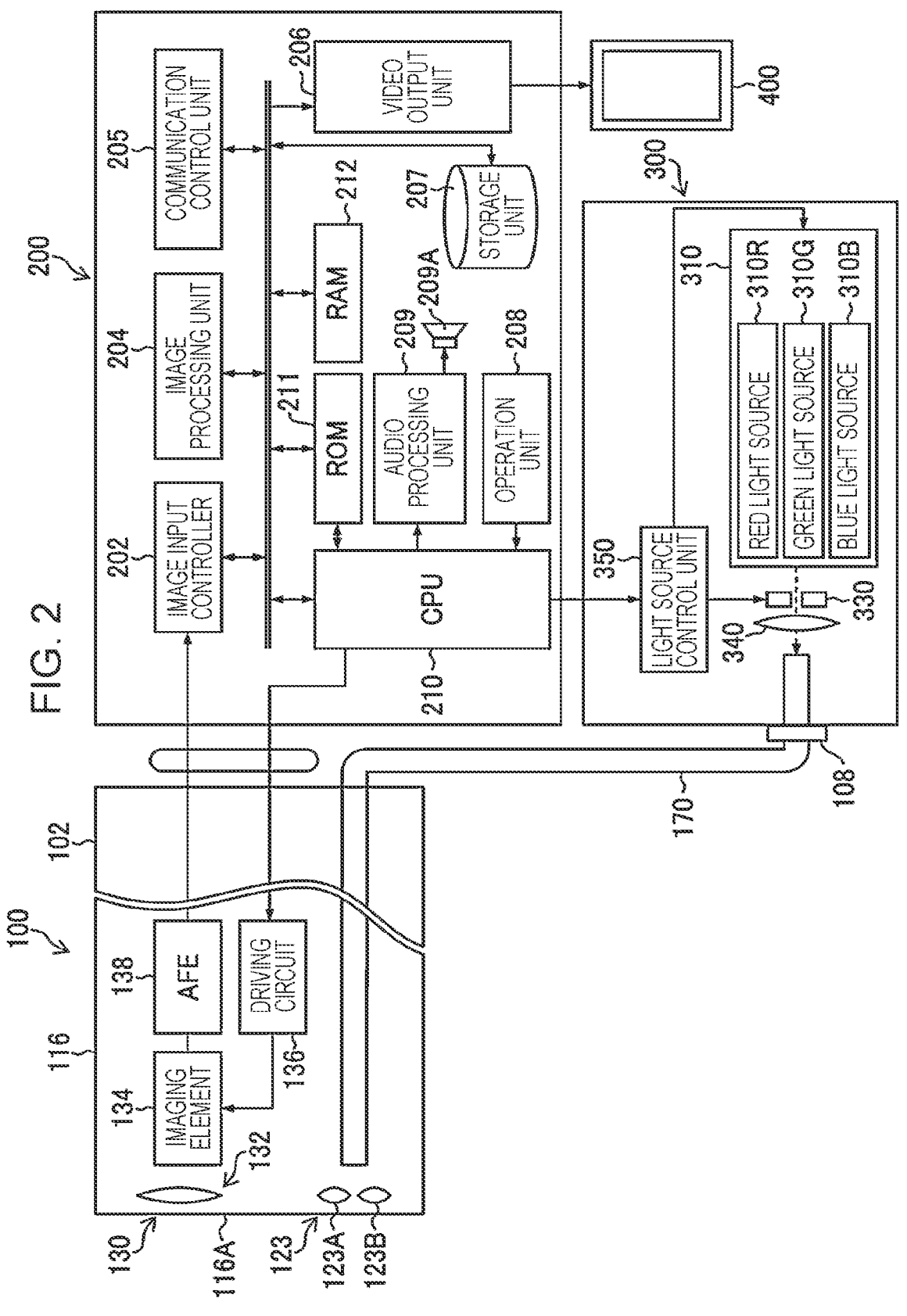
FIG. 2 is a block diagram illustrating an example of a configuration of the endoscope system.

FIG. 2 is a block diagram illustrating an example of a configuration of the endoscope system 10. Examples of configurations of the endoscope 100, the light source device 300, and the processor device 200 will be sequentially described below.

Description of Endoscope

The endoscope 100 includes the imaging unit 130 and the illumination unit 123. The imaging unit 130 is disposed inside the tip rigid part 116. The imaging unit 130 includes an imaging optical system including the imaging lens 132, an imaging element 134, a driving circuit 136, and an analog front end (AFE) 138.

The imaging lens 132 is disposed on a tip-side end face 116A of the tip rigid part 116. The imaging element 134 is disposed behind the imaging lens 132 (at a position closer to the bending part 114 than the tip-side end face 116A). The imaging element 134 is, for example, a complementary metal-oxide semiconductor (CMOS) image sensor. A charge coupled device (CCD) image sensor may be used as the imaging element 134.

The imaging element 134 is, for example, a color imaging element. Thus, a plurality of pixels constituted by a plurality of light-receiving elements including color filters (not illustrated) are two-dimensionally arranged in an array of a specific pattern on a light-receiving surface (imaging surface) of the imaging element 134. Each of the pixels of the imaging element 134 includes a microlens, a color filter, and a photoelectric conversion unit (such as a photodiode). As the color filters, color filters of primary colors including red (R), green (G), and blue (B), for example, are used. The color pattern arrangement form of the color filters is not particularly limited, and may be, for example, a Bayer array or the like.

In addition, the imaging element 134 may include pixels each including a violet color filter corresponding to a violet light source (not illustrated) and/or an infrared filter corresponding to an infrared light source (not illustrated).

The driving circuit 136 supplies various timing signals necessary for an operation of the imaging element 134 to the imaging element 134 on the basis of a control signal transmitted from the processor device 200.

An optical image of a photographic subject that is an observation target is formed on the light-receiving surface of the imaging element 134 through the imaging lens 132. The imaging element 134 converts the optical image of the photographic subject into an electric signal. The electric signal output from the imaging element 134 is processed by the analog front end 138 and is then converted into a digital image signal.

The analog front end 138 includes an amplifier, a filter, and an analog-to-digital converter. The analog front end 138 performs processing such as amplification, noise removal, and analog-to-digital conversion on the output signal of the imaging element 134. The output signal of the analog front end 138 is transmitted to the processor device 200. Note that the imaging element 134, the driving circuit 136, and the analog front end 138 can be configured as a monolithic integrated circuit, and these circuit elements can be mounted on a single imaging chip.

The illumination unit 123 includes the illumination lenses 123A and 123B. The illumination lenses 123A and 123B are disposed at positions adjacent to the imaging lens 132 on the tip-side end face 116A of the tip rigid part 116. An exit end of a light guide 170 is disposed behind the illumination lenses 123A and 123B.

The light guide 170 is inserted in the insertion section 104, the handheld operation section 102, and the universal cable 106 illustrated in FIG. 1. An incident end of the light guide 170 is disposed inside a light guide connector 108 provided at an end of the universal cable 106.

Description of Light Source Device

The light source device 300 supplies illumination light to the light guide 170 through the light guide connector 108. As the illumination light, light in various wavelength ranges according to an observation purpose, such as white light (light in a white wavelength range or light in a plurality of wavelength ranges), light in one or a plurality of specific wavelength ranges, or a combination thereof is selected. Note that each of the specific wavelength ranges is a range narrower than the white wavelength range. The illumination light radiated onto an observation range may be referred to as observation light.

The light source device 300 includes a light source 310 for illumination, a diaphragm 330, a condenser lens 340, and a light source control unit 350. The light source device 300 causes the observation light to be incident to the light guide 170. The light source 310 includes a red light source 310R, a green light source 310G, and a blue light source 310B. The red light source 310R, the green light source 310G, and the blue light source 310B emit red narrow-range light, green narrow-range light, and blue narrow-range light, respectively.

The light source 310 may generate the observation light that is any combination of the red narrow-range light, the green narrow-range light, and the blue narrow-range light. For example, the light source 310 may generate white light by combining the red narrow-range light, the green narrow-range light, and the blue narrow-range light. The light source 310 may generate narrow-range light by combining light of any two colors among the red narrow-range light, the green narrow-range light, and the blue narrow-range light.

The light source 310 may generate narrow-range light by using any one of the red narrow-range light, the green narrow-range light, and the blue narrow-range light. The light source 310 may selectively switch and emit the white light or the narrow-range light. The narrow-range light is synonymous with special light. The light source 310 may include an infrared light source that emits infrared light, an ultraviolet light source that emits ultraviolet light, and the like.

The light source 310 may employ a configuration including a white light source that emits the white light, a filter that allows the white light to pass therethrough, and a filter that allows the narrow-range light to pass therethrough. The light source 310 having such a configuration may selectively emit either the white light or the narrow-range light by switching between the filter that allows the white light to pass therethrough and the filter that allows the narrow-range light to pass therethrough.

The filter that allows the narrow-range light to pass therethrough may include a plurality of filters corresponding to different ranges. The light source 310 may selectively emit a plurality of kinds of narrow-range light in different ranges by selectively switching between the plurality of filters corresponding to the different ranges.

The light source 310 may employ a type, a wavelength range, and the like according to a type of an observation target, an observation purpose, and the like. Examples of the type of the light source 310 include a laser light source, a xenon light source, a light-emitting diode (LED) light source, and the like.

The light guide connector 108 is connected to the light source device 300, so that the incident end of the light guide 170 is disposed on an optical path of light emitted from the condenser lens 340. The observation light emitted from the light source 310 reaches the incident end of the light guide 170 through the diaphragm 330 and the condenser lens 340. The observation light is transmitted to the illumination lenses 123A and 123B through the light guide 170, and is radiated from the illumination lenses 123A and 123B to the observation range.

The light source control unit 350 transmits a control signal to the light source 310 and the diaphragm 330 on the basis of an instruction signal transmitted from the processor device 200. The light source control unit 350 controls an illuminance of the observation light emitted from the light source 310, switching of the observation light, on/off of the observation light, and the like.

Configuration of Processor Device

The processor device 200 includes an image input controller 202, an image processing unit 204, a communication control unit 205, a video output unit 206, and a storage unit 207. The processor device 200 also includes a central processing unit (CPU) 210, a read-only memory (ROM)

211, a random access memory (RAM) 212, an operation unit 208, an audio processing unit 209, and a speaker 209A.

The image input controller 202 acquires an imaging signal from the endoscope 100. The image processing unit 204 processes the imaging signal acquired via the image input controller 202 to generate an endoscopic image of an observation target. Note that the term "image" includes meanings of an image itself and image data representing the image. The image includes both concepts of a moving image and a still image. The imaging signal output from the endoscope 100 may be understood as one aspect of an "endoscopic image".

The image processing unit 204 may perform image quality correction in which digital signal processing such as white balance processing and shading correction processing is applied to the input imaging signal. The image processing unit 204 may be configured by using a dedicated digital signal processing circuit for image processing. In addition, some or all of processing functions of the image processing unit 204 may be implemented as a result of the CPU 210 executing a program. The image processing unit 204 is capable of generating one or a plurality of spectral images on the basis of the imaging signal obtained from the endoscope 100. The image processing unit 204 may also add accessory information defined by the Digital Imaging and Communications in Medicine (DICOM) standard to the endoscopic image.

The storage unit 207 stores an endoscopic image generated using the endoscope 100. The storage unit 207 may store various kinds of information (accessory information) attached to the endoscopic image.

The video output unit 206 transmits various display signals including the image generated using the image processing unit 204, to the monitor 400. The monitor 400 displays an image or the like of the observation target, in accordance with the display signals output from the video output unit 206.

The communication control unit 205 controls communication with an apparatus communicably connected via an in-hospital local area network (LAN), a hospital information system (HIS), or the like. The communication control unit 205 may employ a communication protocol conforming to the DICOM standard.

The CPU 210 functions as an overall control unit that controls each unit in the processor device 200 and integrally controls the entire endoscope system 10. The CPU 210 functions as a memory controller that controls the read-only memory (ROM) 211 and the random access memory (RAM) 212. The ROM 211 stores data such as various programs and control parameters for controlling the operation of the processor device 200.

The RAM 212 is used as a temporary storage area for data in various processes and as a processing area for arithmetic processes using the CPU 210. The RAM 212 storages a program executed by the CPU 210. The RAM 212 can be used as a buffer memory used when an imaging signal or an endoscopic image is acquired.

The operation unit 208 receives a user operation and outputs an instruction signal corresponding to the user operation. The operation unit 208 is configured by using one of or a combination of a plurality of, for example, a keyboard, a mouse, a joystick, a touch panel, a foot switch, and a voice input device. It may be understood that the operation unit 208 includes switches such as the image-capturing button 144 provided in the endoscope 100.

The CPU 210 acquires an instruction signal (user input signal) transmitted from the operation unit 208, and performs processing or control corresponding to the acquired user input signal.

The audio processing unit 209 generates an audio signal representing information to be reported as sound. The speaker 209A converts the audio signal generated by the audio processing unit 209 into sound. Examples of the sound output from the speaker 209A include a message, voice guidance, warning sound, and the like.

The processor device 200 performs various kinds of processing on an endoscopic image generated by using the endoscope 100 or an endoscopic image acquired via the communication control unit 205, and causes the endoscopic image and various kinds of information attached to the endoscopic image to be displayed on the monitor 400. The processor device 200 can also store the endoscopic image and the various kinds of information attached to the endoscopic image in the storage unit 207.

In addition, an endoscopic-image-based diagnosis assistance system that uses AI is implemented in the processor device 200. Although details will be described later, the processor device 200 includes an observation completion determination function of recognizing which part of the inside of the body is in an endoscopic image of an observation target and of determining whether observation is completed for the target part, a display control function of causing a determined result of the observation completion determination to be displayed on the monitor 400, a user input reception function of receiving a user input including an instruction for correcting displayed information of the determined result, and a display correction function of causing corrected content based on the user input to be reflected in the display. The processor device 200 is an example of a "medical image processing apparatus" in the present disclosure. The monitor 400 is an example of a "display device" in the present disclosure. The term "recognition" includes concepts such as identification, discrimination, inference, estimation, detection, and classification.

Overview of Medical Image Processing Apparatus According to First Embodiment

Figure 3:
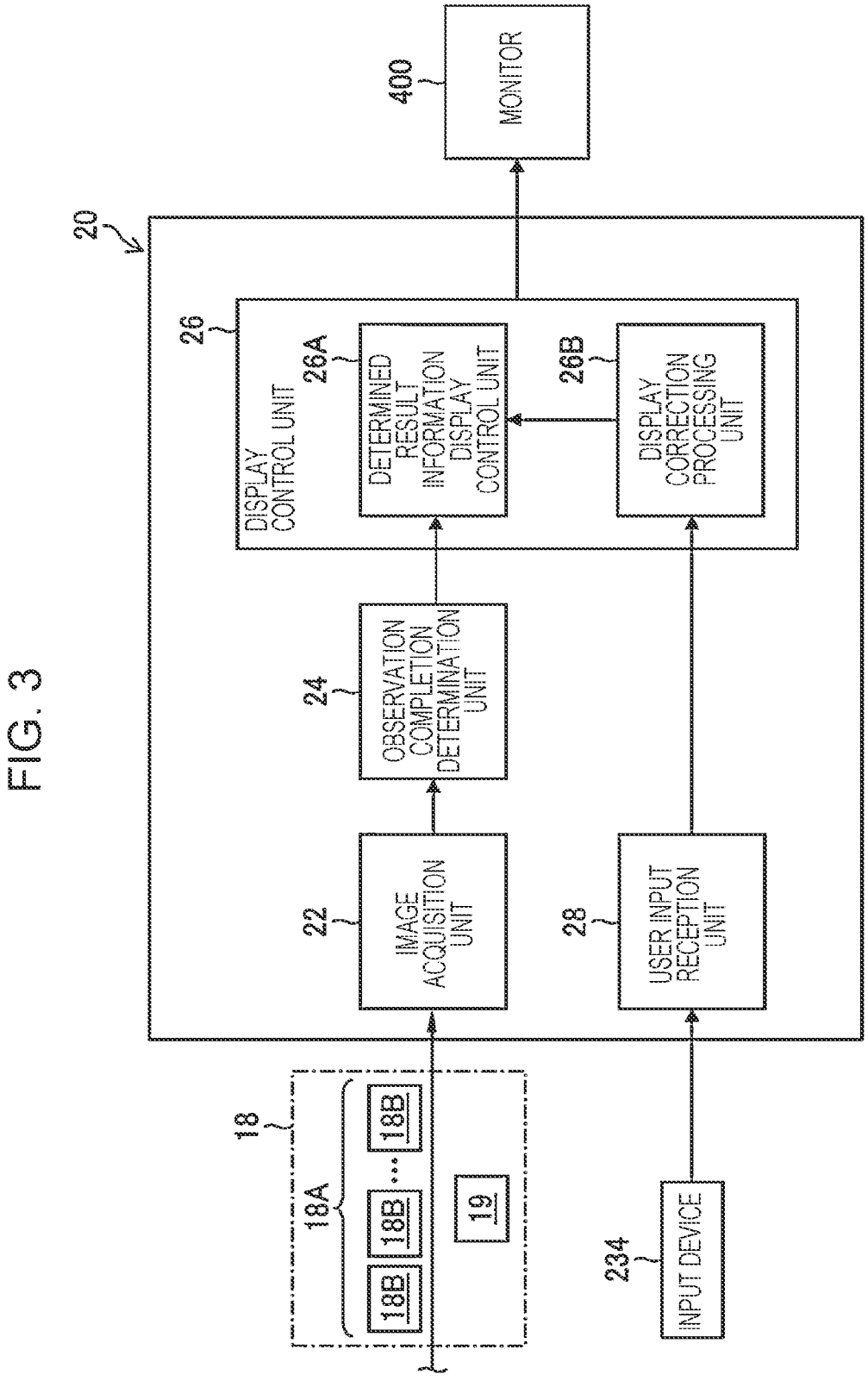
FIG. 3 is a functional block diagram illustrating functions of a medical image processing apparatus according to a first embodiment.

FIG. 3 is a functional block diagram illustrating functions of a medical image processing apparatus 20 according to a first embodiment of the present invention. The medical image processing apparatus 20 includes an image acquisition unit 22, an observation completion determination unit 24, a display control unit 26, and a user input reception unit 28.

The image acquisition unit 22 acquires an endoscopic image 18 captured with the endoscope 100. The endoscopic image 18 may be an image represented by an imaging signal output from the endoscope 100, or may be an image generated through processing performed by the image processing unit 204 illustrated in FIG. 2.

The image input controller 202 illustrated in FIG. 2 may function as the image acquisition unit 22. The image acquisition unit 22 may be configured to include a communication interface for capturing the endoscopic image 18 from an external apparatus via a communication line, or may be configured to include a medium interface for capturing an endoscopic image stored on a portable information storage medium such as a memory card. The communication control unit 205 illustrated in FIG. 2 may function as the image acquisition unit 22.

The image acquisition unit 22 may also be a data input interface and/or a data input terminal that receives an input of the endoscopic image 18 from an internal processing circuit of the processor device 200 illustrated in FIG. 2. For example, the image acquisition unit 22 may be a terminal that receives an input of the endoscopic image 18 generated by the image processing unit 204 illustrated in FIG. 2. The endoscopic image 18 is an example of a "medical image" in the present disclosure.

The image acquisition unit 22 may acquire a moving image 18A constituted by time-series frame images 18B captured by the endoscope 100. In the case where capturing of a still image 19 is performed in response to a still image capturing instruction being input from the user during capturing of the moving image 18A, the image acquisition unit 22 may acquire the still image 19 captured in response to the still image capturing instruction.

The observation completion determination unit 24 is a processing unit that recognizes a scene of the endoscopic image 18 acquired via the image acquisition unit 22 and performs an observation completion determination for a target part. The observation completion determination is a process of determining whether observation is completed for the target part. The observation completion determination unit 24 performs a process of inferring whether a doctor who is the user has actually observed the target part deliberately and has completed the observation for that part.

The observation completion determination unit 24 is configured by using, for example, a part recognizer that performs an image classification process of recognizing a scene of the endoscopic image 18 and assigning a label to the part that is in the endoscopic image 18. For example, the part recognizer is configured by using a trained model of a neural network or the like that has been trained through machine learning such as deep learning. The observation completion determination unit 24 can be configured by using a convolutional neural network (CNN). The observation completion determination unit 24 may be an AI module configured by using an AI model that performs a task of recognizing a target part and making an observation completion determination for the target part on the basis of the endoscopic image 18. The observation completion determination unit 24 may be configured by a combination of a part recognizer and a determiner for determining whether observation is completed, or may be configured by using an AI model that is trained through machine learning so as to output a classification of a part and whether observation is completed, in response to an input of the endoscopic image 18.

The observation completion determination unit 24 may perform a process of recognizing a part and determining whether observation is completed, for each frame image of some or all of the plurality of frame images 18B acquired in time series.

The display control unit 26 controls display content on the monitor 400. That is, the display control unit 26 generates a display signal necessary for a display output to the monitor 400. The display signal includes, in addition to a display signal representing the endoscopic image 18, a display signal for reporting information indicating the determined result of the observation completion determination.

The display control unit 26 includes a determined result information display control unit 26A and a display correction processing unit 26B. The determined result information display control unit 26A generates a display signal for causing determined result information obtained by the observation completion determination unit 24 to be displayed on the monitor 400.

The display signal generated by the determined result information display control unit 26A is output to the monitor 400. In accordance with the display signal from the display control unit 26, the monitor 400 displays information indicating the determined result of the observation completion determination, the endoscopic image 18, and the like.

The user input reception unit 28 receives a user input signal that is input by using an input device 234. The user input signal includes an instruction signal for correcting the information on the observation completion determination result displayed on the monitor 400. The input device 234 corresponds to the operation unit 208 illustrated in FIG. 2. The input device 234 may be, for example, a keyboard, a mouse, a touch panel, a foot switch, a voice input device, or any combination thereof. The user can input various instructions by operating the input device 234.

The display correction processing unit 26B performs a process of correcting information (display content) displayed on the monitor 400 in accordance with the user input signal, and generates a display signal for reflecting the correction content in the display. The display correction processing unit 26B may perform a process of rewriting the information of the determined result output from the observation completion determination unit 24, or may correct the display content on the monitor 400 while holding the information of the determined result of the erroneous determination output from the observation completion determination unit 24 in the apparatus.

The content corrected by the display correction processing unit 26B on the basis of the user input signal is reflected in the display on the monitor 400. The display control unit 26 corresponds to the video output unit 206 illustrated in FIG. 2.

The CPU 210 illustrated in FIG. 2 may function as the observation completion determination unit 24. A combination of the image processing unit 204 and the CPU 210 illustrated in FIG. 2 may appropriately carry out the function of the observation completion determination unit 24 in a distributed manner.

Example of Operation of Medical Image Processing Apparatus 20

Figure 4:
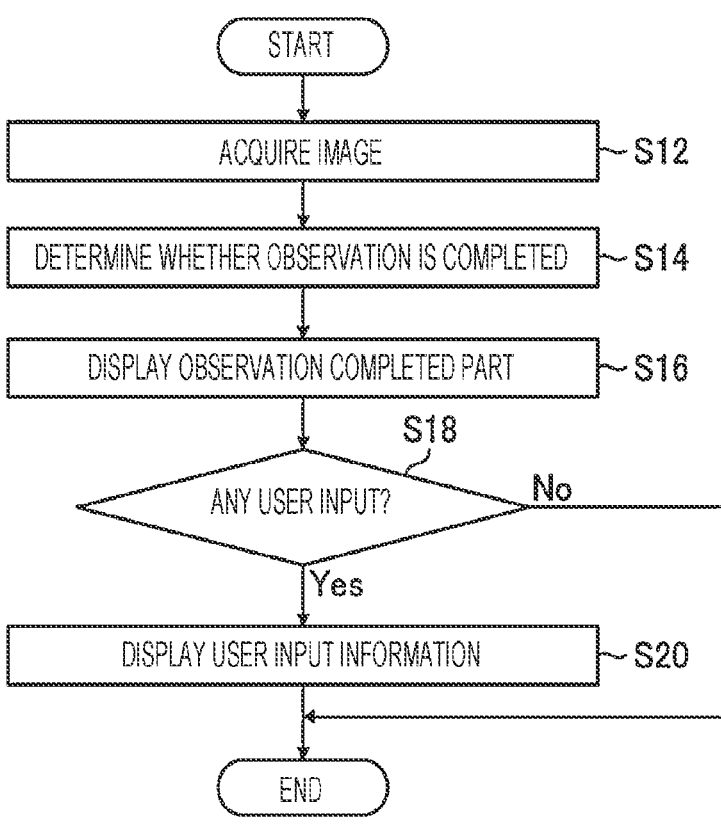
FIG. 4 is a flowchart illustrating an operation of the medical image processing apparatus according to the first embodiment.

FIG. 4 is a flowchart illustrating an operation of the medical image processing apparatus 20. Each step of the flowchart of FIG. 4 is performed as a result of a processor such as the CPU 210 mounted in the medical image processing apparatus 20 executing a program.

In an image acquisition step in step S12, the medical image processing apparatus 20 acquires an endoscopic image.

In an observation completion determination step in step S14, the medical image processing apparatus 20 recognizes an observation target part and determines whether observation of the part is completed.

In an observation completed part display step in step S16, based on the determined result of the observation completion determination, the medical image processing apparatus 20 causes information on the observation completed part for which it is determined that observation has completed to be displayed on the monitor 400.

In step S18, the medical image processing apparatus 20 determines whether there is a user input including an instruction for correcting the display content of the observation completed part. In response to the user inputting an instruction for correcting the display, the medical image processing apparatus 20 causes the process to proceed to a user input information display step in step S20.

In step S20, the medical image processing apparatus 20 reflects the correction content input by the user in the display on the monitor 400.

If no instruction for correcting the display is input from the user in step S18, the medical image processing apparatus 20 skips step S20, maintains the display of the information of the observation completed part indicated by the determined result of the observation completion determination, and ends the flowchart of FIG. 4. The medical image processing apparatus 20 may perform the process according to the flowchart in FIG. 4 on each of the plurality of frame images 18B sequentially acquired in time series.

The operation method of the medical image processing apparatus 20 illustrated in the flowchart of FIG. 4 may be understood as a diagnosis assistance method performed by the medical image processing apparatus 20, or may be understood as an image processing method performed by the medical image processing apparatus 20.

First Example of Displayed Image

Figure 5:
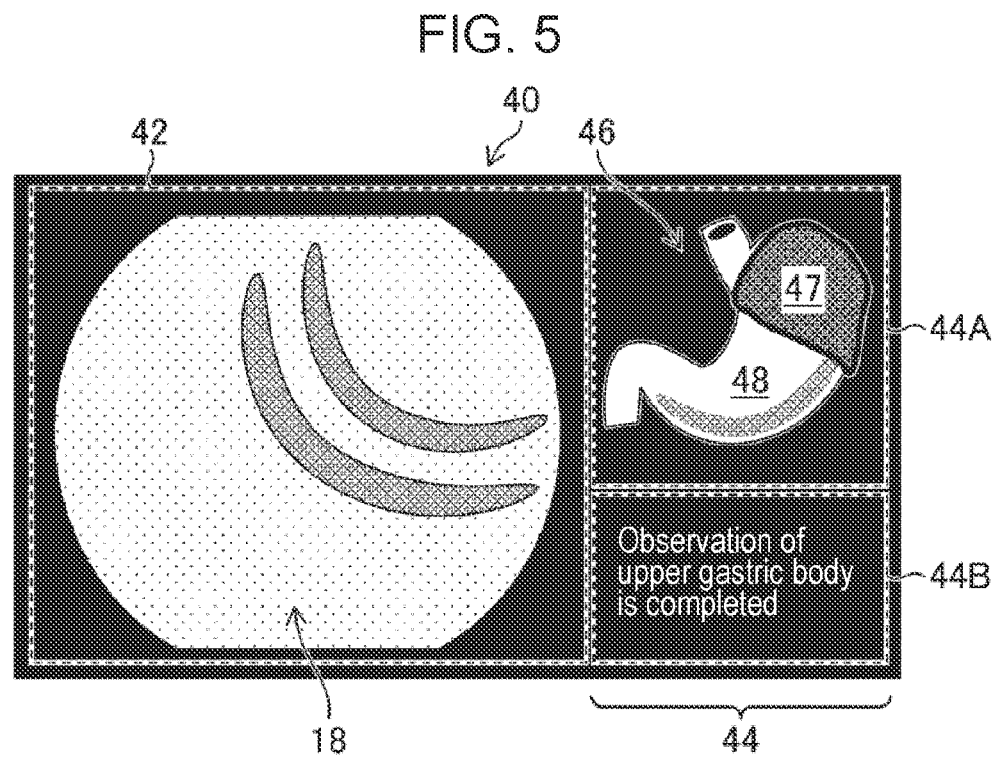
FIG. 5 is a first example of a displayed image that is displayed on a screen of a monitor.

FIG. 5 is a first example of a displayed image that is displayed in a screen 40 of the monitor 400. FIG. 5 illustrates an example of an endoscopic image captured with a flexible video gastroduodenoscope. FIG. 5 is an example of an observation image of the upper gastric body. The screen 40 of the monitor 400 includes a main screen 42 and a sub-screen 44. The endoscopic image 18 that is an observation image is displayed in the main screen 42. In the main screen 42, the endoscopic image 18 being captured is displayed in real time as a moving image. The main screen 42 functions as an observation image display region.

The sub-screen 44 displays information on an observation completed part. The user operates the endoscope 100 while viewing an inside-body image (endoscopic image 18) displayed in the main screen 42. The observation completion information of the part is displayed in the sub-screen 44. The medical image processing apparatus 20 determines whether observation of a certain part is completed on the basis of scene recognition processing on the endoscopic image 18, and causes the determined result to be displayed in the sub-screen 44 in a display form such as a diagram and/or a list. The main screen 42 is an example of a "first display region" in the present disclosure. The sub-screen 44 is an example of a "second display region" in the present disclosure.

In a first sub-screen 44A in FIG. 5, a schematic image 46 schematically representing the stomach which is an observation target organ is presented, and an observation completed part 47 and an observation incomplete part 48 are displayed in different colors. FIG. 5 illustrates a display example in the case where it is determined that observation of the upper gastric body is completed. The stomach is an example of a "part of a human body" in the present disclosure, and the schematic image 46 is an example of a "model figure" in the present disclosure.

In a second sub-screen 44B, text information indicating the determined result obtained by the observation completion determination unit 24 is displayed. That is, in the second sub-screen 44B, information on the part recognized as an observation target and the determined result information indicating the determined result of whether observation is completed are displayed as information of a character string. Here, an example is illustrated in which a display "upper gastric body" serving as the part information and a display "observation completed" serving as the determined result information are displayed.

Second Example of Displayed Image

Figure 6:
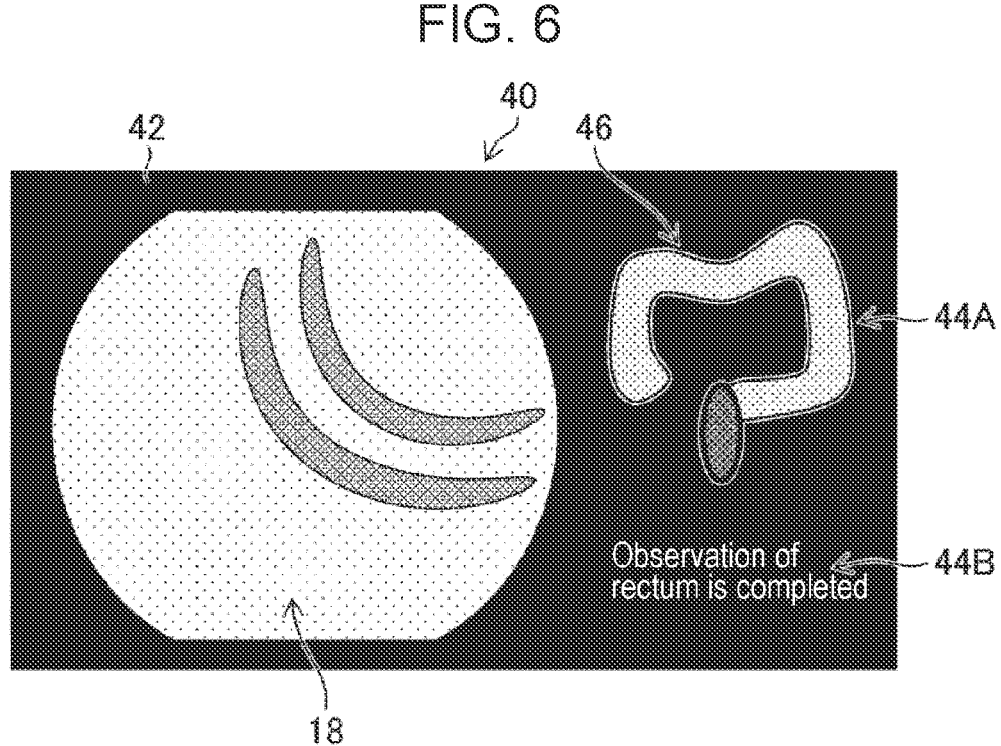
FIG. 6 is a second example of the displayed image that is displayed on the screen of the monitor.

FIG. 6 is a second example of the displayed image that is displayed in the screen 40 of the monitor 400. FIG. 6 illustrates an example of an observation image of the rectum. FIG. 6 illustrates a display example in the case where it is determined that observation of the rectum is completed in the colonoscopy. In the first sub-screen 44A in FIG. 6, the schematic image 46 of the large intestine is displayed, and a state in which a part that is the rectum is set as the observation completed part 47 is illustrated. In the second sub-screen 44B in FIG. 6, an example is presented in which text information "rectum" serving as the information on the part recognized as the observation target and "observation completed" serving as the determined result information are displayed.

Third Example of Displayed Image

Figure 7:
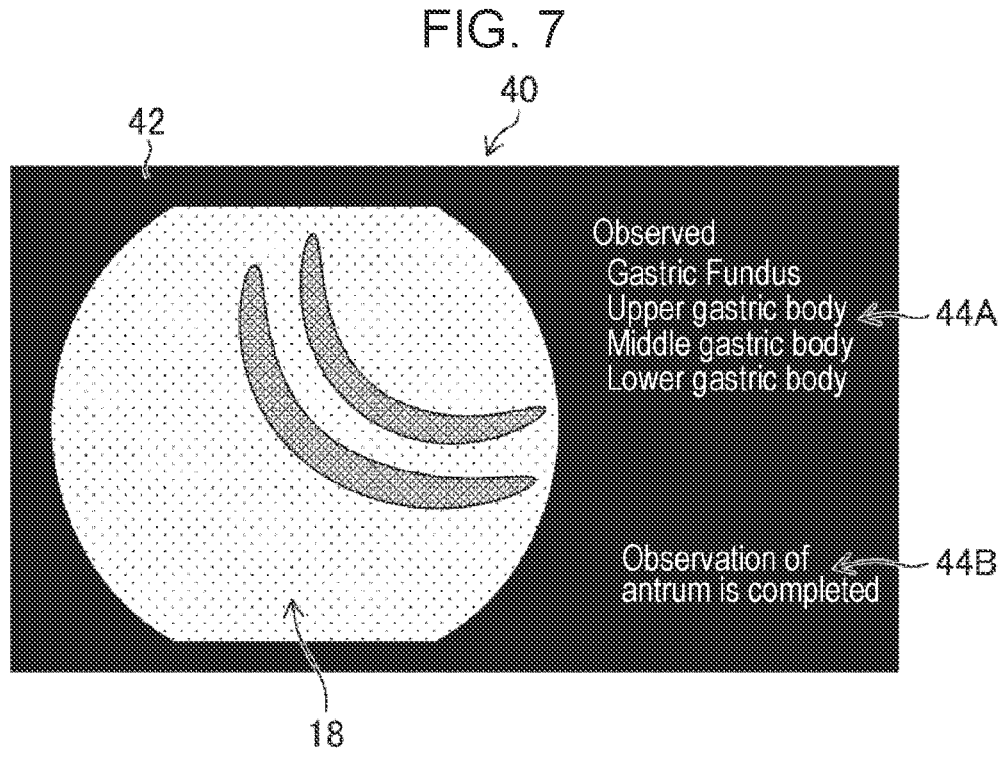
FIG. 7 is a third example of the displayed image that is displayed on the screen of the monitor.

FIG. 7 is a third example of the displayed image that is displayed in the screen 40 of the monitor 400. Instead of the display using the schematic image 46 described in FIG. 5, information on observed parts may be listed and displayed as text information as illustrated in FIG. 7.

In FIG. 7, a list of observed parts is displayed in the first sub-screen 44A, and information on the part currently observed is displayed in the second sub-screen 44B. In FIG. 7, the gastric fundus, the upper gastric body, the middle gastric body, and the lower gastric body are listed as the observed parts.

The endoscopic image 18 displayed in the main screen 42 in FIG. 7 is an observation image of the antrum of the stomach. In response to the observation completion determination unit 24 determining that observation of the antrum is completed, text information indicating that it is determined that observation of the antrum is completed is displayed in the second sub-screen 44B.

In FIG. 7, a list of observed parts is displayed in the first sub-screen 44A, and information on the part currently observed is displayed in the second sub-screen 44B. In FIG. 7, the gastric fundus, the upper gastric body, the middle gastric body, and the lower gastric body are listed as the observed parts.

The endoscopic image 18 displayed in the first sub-screen 44A in FIG. 7 is an observation image of the antrum of the stomach. In response to the observation completion determination unit 24 determining that observation of the antrum is completed, text information indicating that it is determined that observation of the antrum is completed is displayed in the second sub-screen 44B.

Fourth Example of Displayed Image

Figure 8:
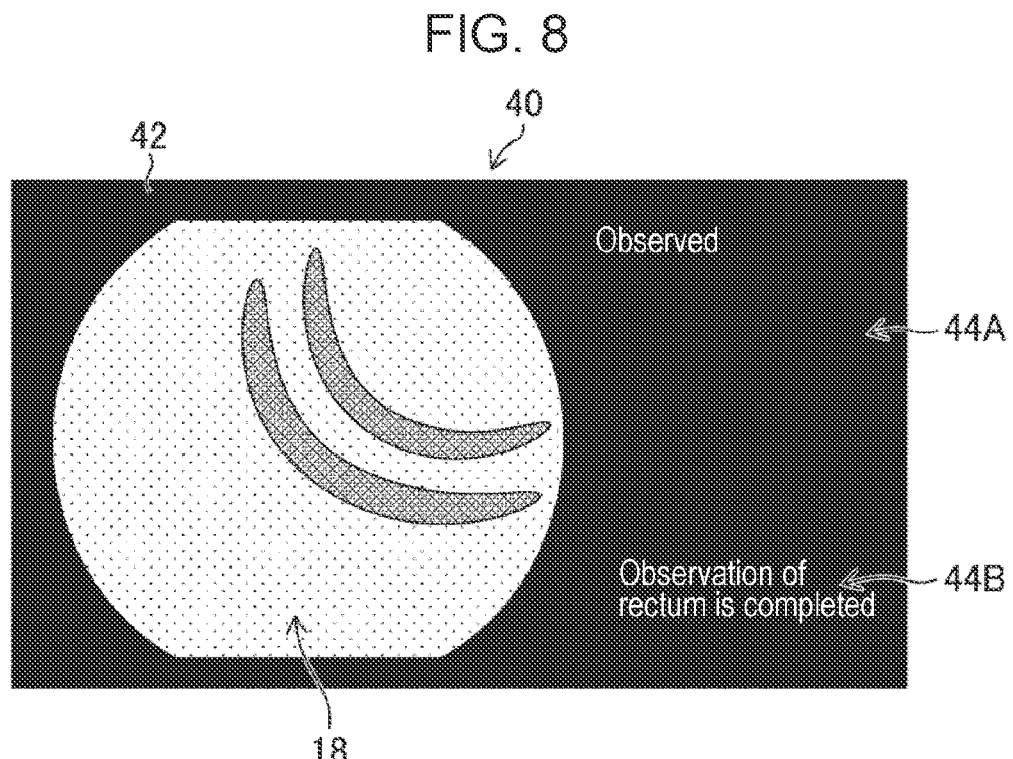
FIG. 8 is a fourth example of the displayed image that is displayed on the screen of the monitor.

FIG. 8 is another example of the displayed image that is displayed in the screen 40 of the monitor 400. In FIG. 8, there is no observed part, and the information on the observed part is blank in the first sub-screen 44A. FIG. 8 illustrates a state when the observation completion determination unit 24 determines that observation of the rectum is completed. In this case, text information indicating that it is determined that observation of the rectum is completed is displayed in the second sub-screen 44B.

First Example of Correcting Display Based on User Input

Figure 9:
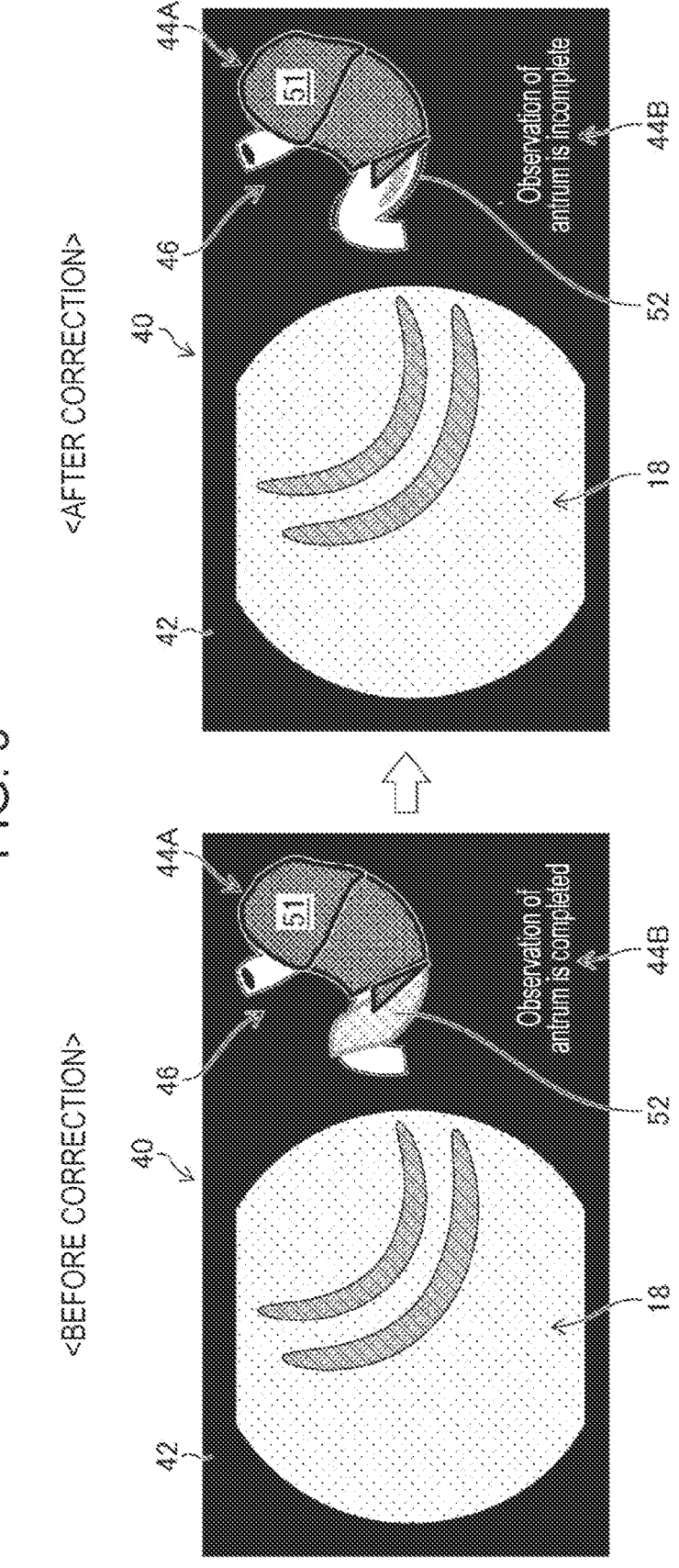
FIG. 9 is an example of the displayed image in the case where a display of observation completion information based on a determined result of an observation completion determination is corrected to observation incompletion information.

FIG. 9 is an example of the displayed image in the case where the display of the observation completion information based on the determined result of the observation completion determination is corrected to observation incompletion information. In FIG. 9, the left side illustrates the display content yet to be corrected, and the right side illustrates the corrected display content.

The observation completion determination unit 24 determines that observation is completed for the antrum, and a display reporting the completion of observation of the antrum is performed in the screen 40 of the monitor 400 as illustrated in the left diagram in FIG. 9.

In the schematic image 46 in the first sub-screen 44A, a region block 51 corresponding to a part confirmed to be already observed is displayed, for example, by being filled with a display color (for example, blue) indicating the observation completed part. If it is newly determined that observation of the part that is the antrum is completed this time, a region block 52 corresponding to the antrum in the schematic image 46 is displayed, for example, by being filled with a display color (for example, orange) indicating the part newly determined to be the observation completed part. In addition, text information indicating that it is determined that observation of the antrum is completed is displayed in the second sub-screen 44B.

In the display state illustrated in the left diagram in FIG. 9, if a predetermined time elapses without any input of a correction instruction by the user, the observation completion information of the antrum is confirmed to be correct, and the display color of the region block 52 changes from orange to blue. The "predetermined time" may be, for example, about several seconds. Here, an example has been described in which the display of the observation completed part in the schematic image 46 is changed to the confirmed display which is "blue" through "orange". However, the display need not go through such a color change. The display content of the sub-screen 44 illustrated in the left diagram of FIG. 9 is an example of an "observation completed display" in the present disclosure.

In contrast to the display illustrated in the left diagram of FIG. 9, if the observation of the antrum is incomplete in the actual observation performed by the user, the user can operate the input device 234 to input an instruction for correcting the content of the display indicating "observation completed" for the antrum to a display indicating "observation incomplete".

A method of inputting the correction instruction used by the user may be an operation of inputting text for correcting the text information in the second sub-screen 44B, or may be an operation of selecting "observation incomplete" from a menu such as a pull-down menu that presents candidates for correction.

In response to the user input for correcting the display content being performed in this manner, the corrected content based on the user input is reflected, and the display content is changed from the display illustrated in the left diagram of FIG. 9 to the corrected display illustrated in the right diagram of FIG. 9. In the right diagram of FIG. 9, the region block 52 corresponding to the antrum in the schematic image 46 is displayed in a display color (for example, gray) indicating that observation is incomplete, and text information indicating that "observation incomplete" is displayed for the antrum in the second sub-screen 44B. In the schematic image 46 in the right diagram of FIG. 9, a frame line of the region block 52 is illustrated as a broken line for convenience of illustration in order to clearly indicate the region block 52 for which the display has been corrected. However, such a frame line need not be displayed in the actual screen display. The display content of the sub-screen 44 illustrated in the right diagram of FIG. 9 is an example of "observation incomplete display" in the present disclosure.

Second Example of Correcting Display Based on User Input

Figure 10:
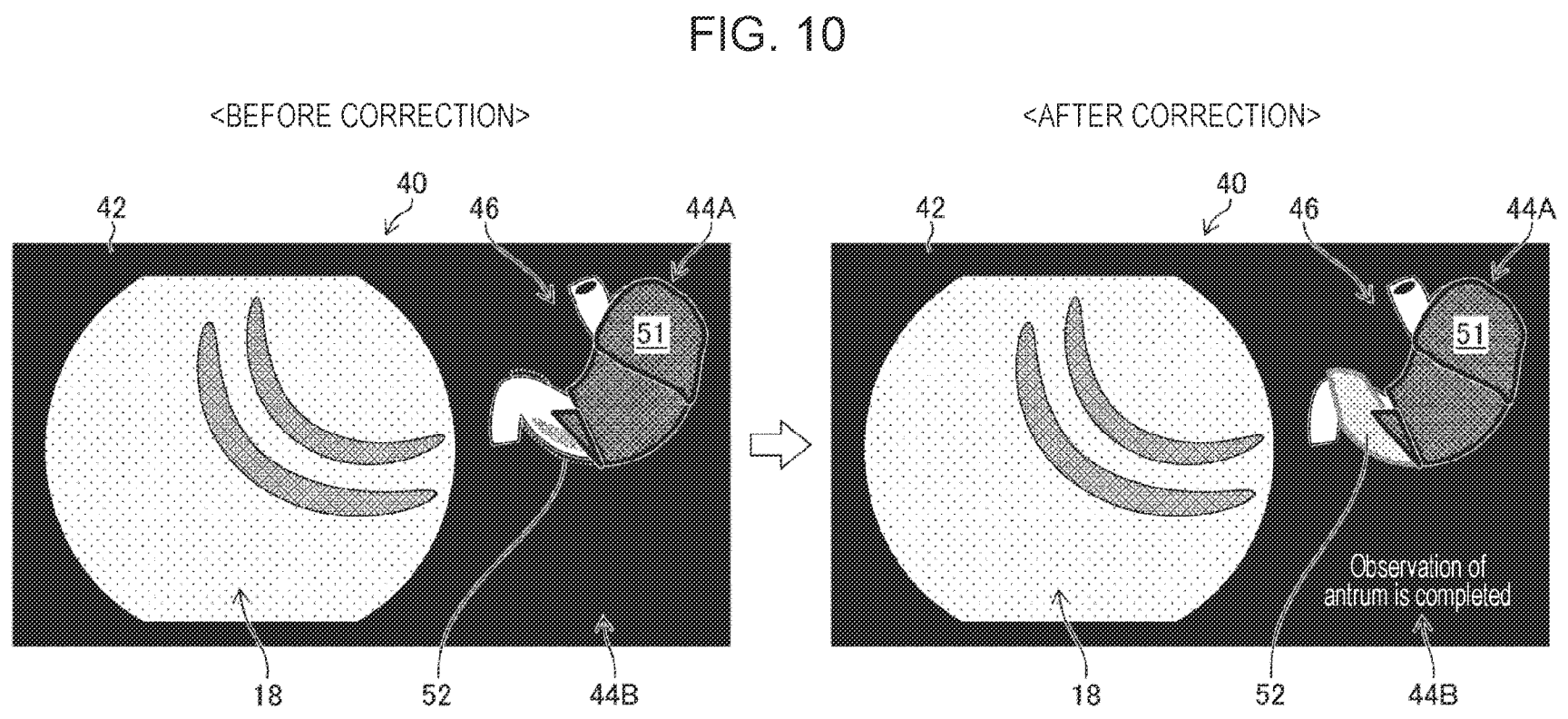

FIG. 10 is an example of the displayed image in the case where the display of the observation incompletion information based on the determined result of the observation completion determination is corrected to the observation completion information. The observation completion determination unit 24 determines that observation is incomplete for the antrum, and the observation completion information is not reported for the antrum in the screen 40 of the monitor 400 as illustrated in the left diagram of FIG. 10. In the schematic image 46 in FIG. 10, the frame line of the region block 52 is illustrated as a broken line for convenience of illustration in order to clearly indicate that the region block 52 corresponding to the antrum is "observation incomplete". However, such a frame line is not displayed in actual screen display.

In contrast to the display illustrated in the left diagram of FIG. 10, if the observation is completed for the antrum in the actual observation performed by the user, the user can operate the input device 234 to input an instruction for correcting the content of the display indicating "observation incomplete" for the antrum to a display indicating "observation completed".

In response to the user input for correcting the display content being performed in this manner, the content corrected based on the user input is reflected, and the display content is changed from the display illustrated in the left diagram of FIG. 10 to the corrected display illustrated in the right diagram of FIG. 10. In the right diagram of FIG. 10, the region block 52 corresponding to the antrum in the schematic image 46 is displayed in a display color (for example, orange or blue) indicating that observation is completed, and text information indicating that "observation completed" is displayed for the antrum in the second sub-screen 44B.

Third Example of Correcting Display Based on User Input

Figure 11:
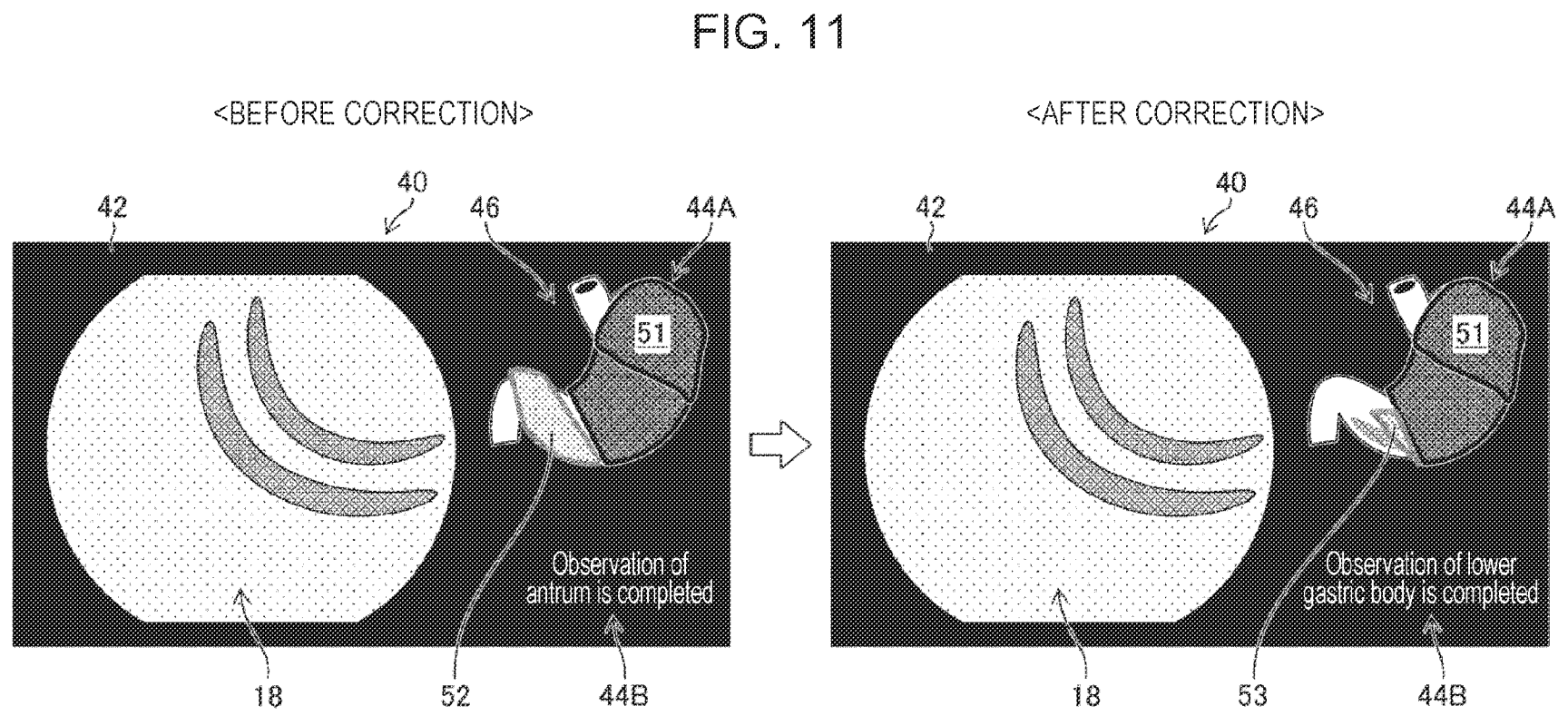

FIG. 11 is an example of the displayed image in the case where a display of the observation completion information for a part based on the determined result of the observation completion determination is corrected to the observation completion information for another part. The observation completion determination unit 24 determines that observation is completed for the antrum, and the observation completion information is reported for the antrum in the screen 40 of the monitor 400 as illustrated in the left diagram of FIG. 11. In addition, in the schematic image 46 in FIG. 11, the lower gastric body is displayed to indicate that observation is incomplete.

In contrast to the display illustrated in the left diagram of FIG. 11, if the observation of the antrum is incomplete but observation of the lower gastric body is completed in the actual observation performed by the user, the user can operate the input device 234 to input an instruction for correcting the display of the information on the observation completed part from the "antrum" to the "lower gastric body".

In response to the user input for correcting the display content being performed in this manner, the corrected content based on the user input is reflected, and the display content is changed from the display illustrated in the left diagram of FIG. 11 to the corrected display illustrated in the right diagram of FIG. 11. In the right diagram of FIG. 11, a region block 53 corresponding to the lower gastric body in the schematic image 46 is displayed in a display color (for example, orange or blue) indicating that observation is completed, and the region block 52 corresponding to the antrum is displayed in a display color (for example, gray) indicating that observation is incomplete.

In addition, in the second sub-screen 44B, text information indicating "observation is completed" for the lower gastric body is displayed.

As illustrated in FIGS. 9 to 11, according to the medical image processing apparatus 20 according to the present embodiment, in the case where the determined result of the observation completion determination is incorrect, it is possible to switch information in the display between "observation completed" or "observation incomplete" based on the determined result, change information on the observation completed part, or the like.

Example of Determination Criteria of Observation Completion Determination

For example, conditions below can be used as determination criteria used when the observation completion determination unit 24 determines that observation is completed.

[Condition 1] A mark (landmark) for a target part is in an image.

[Condition 2] The target part is observed for a predetermined period or more.

[Condition 3] The target part is in a central portion of the image.

The observation completion determination unit 24 determines that observation is completed when at least one condition among these conditions 1 to 3 is met. The observation completion determination unit 24 may determine that observation is completed when two or more conditions among these plurality of conditions are met.

The "mark" in the condition 1 may be an anatomical landmark, and may be, for example, a pattern specific to a mucous membrane and/or a characteristic structure of the part. The mark is set for each part. In response to recognizing the mark from the endoscopic image 18, the observation completion determination unit 24 may determine that observation is completed for the part associated with the mark.

Figures 12, 13:
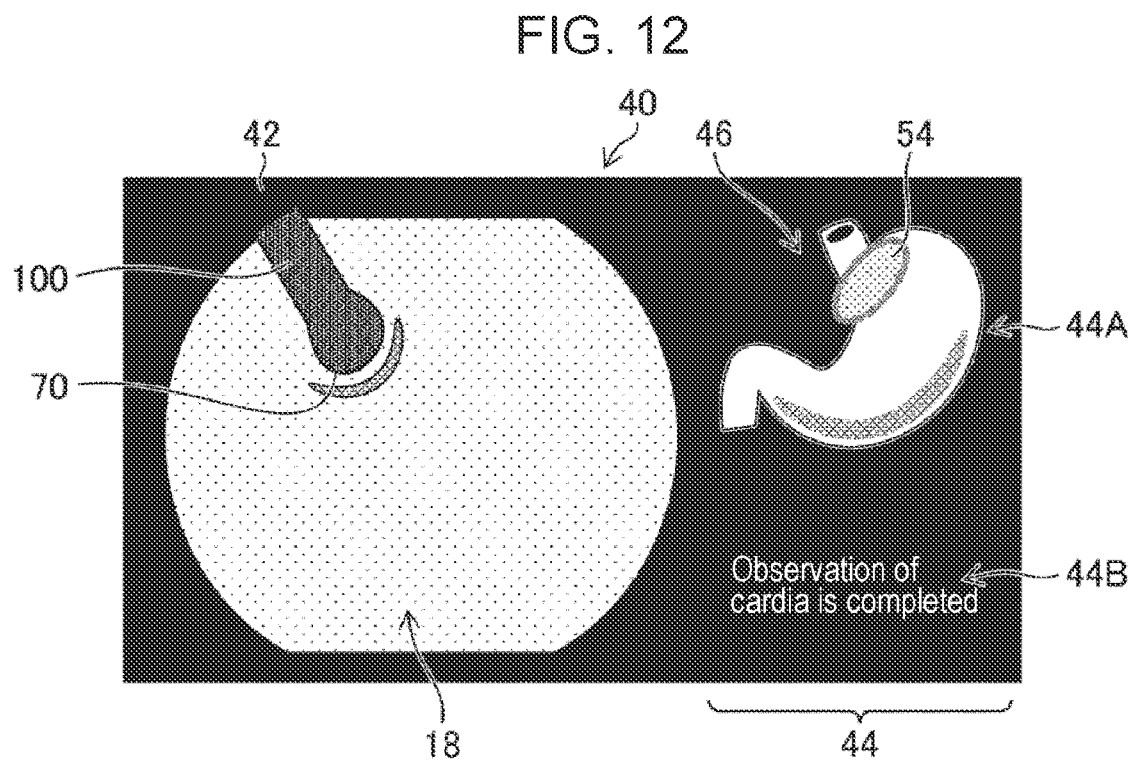
FIG. 12 is an example of an observation image obtained when the cardia of the stomach is observed.
FIG. 13 is an example of another observation image obtained when the cardia of the stomach is observed.

FIG. 12 is an example of an observation image obtained when the cardia of the stomach is observed. FIG. 12 illustrates an example of the case where it is determined that observation is completed because the condition 1 is met. Since the cardia is observed with the bending part 114 of the endoscope 100 being bent, a hole 70 of the cardia and the endoscope 100 are in the endoscopic image 18 during observation. The hole 70 of the cardia and the endoscope 100 may serve as the mark for the cardia. The observation completion determination unit 24 recognizes (detects) the mark from the endoscopic image 18, and determines that observation is completed if the mark is present in the image.

In the case where the endoscopic image 18 as illustrated in the main screen 42 in FIG. 12 is obtained, the observation completion determination unit 24 may determine that observation is completed for the cardia because the condition 1 is met. In response to the observation completion determination unit 24 determining that observation is completed for the cardia, a region block 54 corresponding to the cardia in the schematic image 46 in the first sub-screen 44A is displayed in a display color indicating that observation is completed. In addition, text information indicating that the observation of the cardia is completed is displayed in the second sub-screen 44B.

As for the condition 2, the observation completion determination unit 24 recognizes a part from the endoscopic image 18, and determines that observation is completed if the same part is present in the image for a predetermined period or longer. For example, the observation completion determination unit 24 may perform, for each of the frame images 18B acquired in time series at specific time intervals, detection of a part on the frame image 18B, and determine that observation of that part is completed if a predetermined number or more of frame images 18B in which the same part has been detected are consecutive. The "predetermined period" in the condition 2 can be set to an appropriate value in advance, and may be, for example, about several seconds.

FIG. 13 is another example of an observation image obtained when the cardia of the stomach is observed. FIG. 13 illustrates an example of the case where it is determined that observation is completed because the condition 3 is met.

In FIG. 13, the hole 70 of the cardia is in the central portion of the endoscopic image 18. For example, the observation completion determination unit 24 detects a target mark from the endoscopic image 18, recognizes a position of the mark in the image and the type (classification) of the part, and determines whether the mark is present in the central portion of the image. If the mark for the target part is present in the central portion of the endoscopic image 18, the observation completion determination unit 24 may determine that observation of that part is completed.

The cardia is an example of a "specific part" in the present disclosure, and the hole 70 of the cardia is an example of a "mark" in the present disclosure. The condition 1 is an example of a "first condition" in the present disclosure. The condition 2 is an example of a "second condition" in the present disclosure. The condition 3 is an example of a "third condition" in the present disclosure.

The determination criteria of the observation completion determination are not limited to the conditions 1 and 3. For example, in the case where capturing of a still image is performed in response to an operation on the image-capturing button 144 of the endoscope 100, the observation completion determination unit 24 may determine that observation of a part that is a photographic subject of the still image is completed. That is, the observation completion determination unit 24 may receive an input of an image-capturing instruction signal indicating an image-capturing timing of a still image, and may determine, in the case of receiving the input of the image-capturing instruction signal, that observation is completed for the part that is an image-capturing target of the still image. By using a condition 4 that "Capturing of a still image has been performed" as the determination criteria of the observation completion determination, the observation completion determination unit 24 may determine that observation is completed when one or more conditions among the conditions 1 to 4 are met.

Example of Hardware Configuration of Medical Image Processing Apparatus 20

Figure 14:
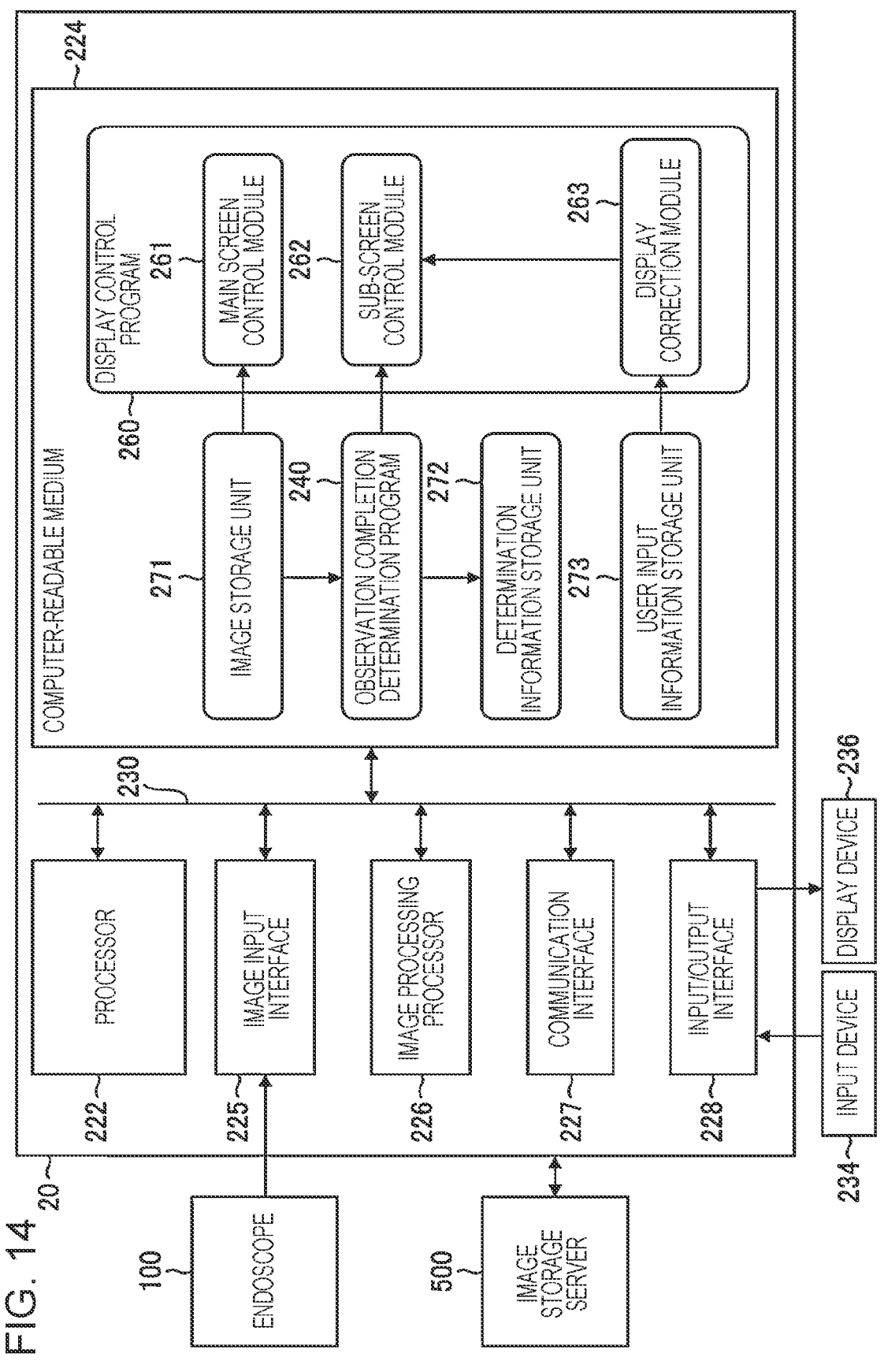
FIG. 14 is a block diagram illustrating an example of a hardware configuration of the medical image processing apparatus according to the first embodiment.

FIG. 14 is a block diagram illustrating, as an example, a hardware configuration of the medical image processing apparatus 20. The medical image processing apparatus 20 is not limited to a form of being mounted in the processor device 200, and can be applied to an information processing apparatus different from the processor device 200. For example, the processing functions of the medical image processing apparatus 20 may be implemented in an image processing server or the like connected to an in-hospital network.

The medical image processing apparatus 20 can be implemented by a computer system configured by using one or a plurality of computers. That is, the medical image processing apparatus 20 is implemented by installing a program in a computer.

The medical image processing apparatus 20 includes a processor 222, a computer-readable medium 224 that is non-transitory and tangible, an image input interface 225, an image processing processor 226, a communication interface 227, an input/output interface 228, and a bus 230.

The processor 222 includes a CPU. The processor 222 may include a graphics processing unit (GPU). The processor 222 is connected to the computer-readable medium 224, the image input interface 225, the image processing processor 226, the communication interface 227, and the input/output interface 228 through the bus 230. The medical image processing apparatus 20 may further include the input device

234 and a display device 236. The input device 234 and the display device 236 are connected to the bus 230 through the input/output interface 228.

The computer-readable medium 224 includes a memory that is a main memory device and a storage that is an auxiliary memory device. The computer-readable medium 224 may be, for example, a semiconductor memory, a hard disk drive (HDD) device, a solid state drive (SSD) device, or a combination of a plurality of these.

The image input interface 225 may function as the image acquisition unit 22 illustrated in FIG. 3. The medical image processing apparatus 20 is connected to the endoscope 100 through the image input interface 225.

The image processing processor 226 is a processor dedicated to image processing and corresponding to the image processing unit 204 illustrated in FIG. 2.

The communication interface 227 corresponds to the communication control unit 205 illustrated in FIG. 2. The medical image processing apparatus 20 is connected to a communication line (not illustrated) through the communication interface 227. The communication line may be, for example, a local area network (LAN) created in a hospital. The communication network in a hospital is referred to as an in-hospital network. The in-hospital network may be further connected to a wide area network such as the Internet via a router. An image storage server 500 such as a Picture Archiving and Communication Systems (PACS) server is connected to the in-hospital network.

The PACS server is a computer that stores and manages various kinds of data including medical images captured using various modalities, and includes a large-capacity external storage device and database management software. The PACS server communicates with other apparatuses via the in-hospital network to transmit and receive various kinds of data including image data. The PACS server may be a DICOM server that operates on the basis of the DICOM protocol.

The medical image processing apparatus 20 may acquire an endoscopic image from the image storage server 500 connected through the communication interface 227.

An observation completion determination program 240 and a display control program 260 are stored on the computer-readable medium 224. The computer-readable medium 224 includes an image storage unit 271, a determination information storage unit 272, and a user input information storage unit 273. The computer-readable medium 224 may store an image processing program (not illustrated) including instructions for causing the processor 222 to execute a portion or entirety of the process of the image processing unit 204 described in FIG. 2.

The image storage unit 271 is a storage area for storing an endoscopic image acquired via the image input interface 225 or the communication interface 227.

The observation completion determination program 240 is a program including instructions for causing the processor 222 to execute the process of the observation completion determination unit 24 described in FIG. 3.

The display control program 260 is a program including instructions for causing the processor 222 to execute the process of the display control unit 26 described with reference to FIG. 3. The display control program 260 includes a main screen control module 261, a sub-screen control module 262, and a display correction module 263.

The main screen control module 261 is a program module that performs control related to a display in the main screen 42. The sub-screen control module 262 is a program module that performs control related to a display in the sub-screen 44. The sub-screen control module 262 includes instructions for causing the processor 222 to execute the process of the determined result information display control unit 26A described in FIG. 3. The display correction module 263 is a program module including instructions for causing the processor 222 to execute the process of the display correction processing unit 26B described in FIG. 3. A portion or entirety of the display control program 260 may be incorporated in the observation completion determination program 240.

The determination information storage unit 272 is a storage area that stores information of the determined result obtained through execution of the observation completion determination program 240. The user input information storage unit 273 is a storage area that stores user input information input from the input device 234 via the input/output interface 228. The computer-readable medium 224 stores, for each type of examination performed using the endoscope system 10, information on a target organ and a plurality of sub-parts (sub-regions) to be observed in the series of examination. Specifically, for example, in the case where an examination for observing all the internal parts of the stomach is performed, the cardia, the gastric fundus, the gastric angular region, the upper gastric body, the middle gastric body, the lower gastric body, the antrum, the pyloric region, and the like are set as parts to be observed.

Although sub-parts of the stomach are used as an example herein, classification labels of the parts are not limited to this example. For example, the target part subjected to the observation completion determination is not limited to a single organ and may be a plurality of organs. For example, the observation completion determination may be performed on not only the stomach but also parts in an examination range including the esophagus and the duodenum. As the parts of the esophagus, for example, classifications such as the upper esophagus, the mid-esophagus, the lower esophagus are used. As parts of the duodenum, for example, classifications such as the duodenal bulb and the postbulbus of the duodenum are used.

The display device 236 may be, for example, a liquid crystal display device, an organic electro-luminescence (OEL) display device, a projector, or any combination thereof. In addition to a recognition result, the display device 236 may display an image that is a target of processing and various kinds of information such as various kinds of setting information necessary for the processing. The display device 236 corresponds to the monitor 400 illustrated in FIG. 2. The display device 236 is an example of a "display device" in the present disclosure.

The determined result of the observation completion determination performed by the observation completion determination program 240 is transmitted to the sub-screen control module 262 and is displayed in the sub-screen 44. The display correction module 263 receives a user input from the input device 234 and corrects the display content of the sub-screen 44 in accordance with the user input.

The medical image processing apparatus 20 according to the present embodiment can automatically determine whether observation is completed for a target part from the endoscopic image 18 that is being observed and cause information on the observation completed part to be displayed on the monitor 400. In addition, in the case where the determined result of the observation completion determination performed on the part by using the AI is different from the determination made by a person (doctor) who is the user, the medical image processing apparatus 20 according to the present embodiment can correct the display indicating the result of the observation completion determination in response to an interaction of the user.

In an examination process in which a plurality of parts are sequentially observed, the medical image processing apparatus 20 can determine an observation behavior of the doctor from the acquired endoscopic images 18 and provide information on the observation completed part in real time. Thus, in an examination that requires thorough observation of the plurality of parts, the medical image processing apparatus 20 can timely provide information on an observation completed part and information on an observation incomplete part to the user and consequently suppress oversight of a part to be observed.

Second Embodiment

Figure 15:
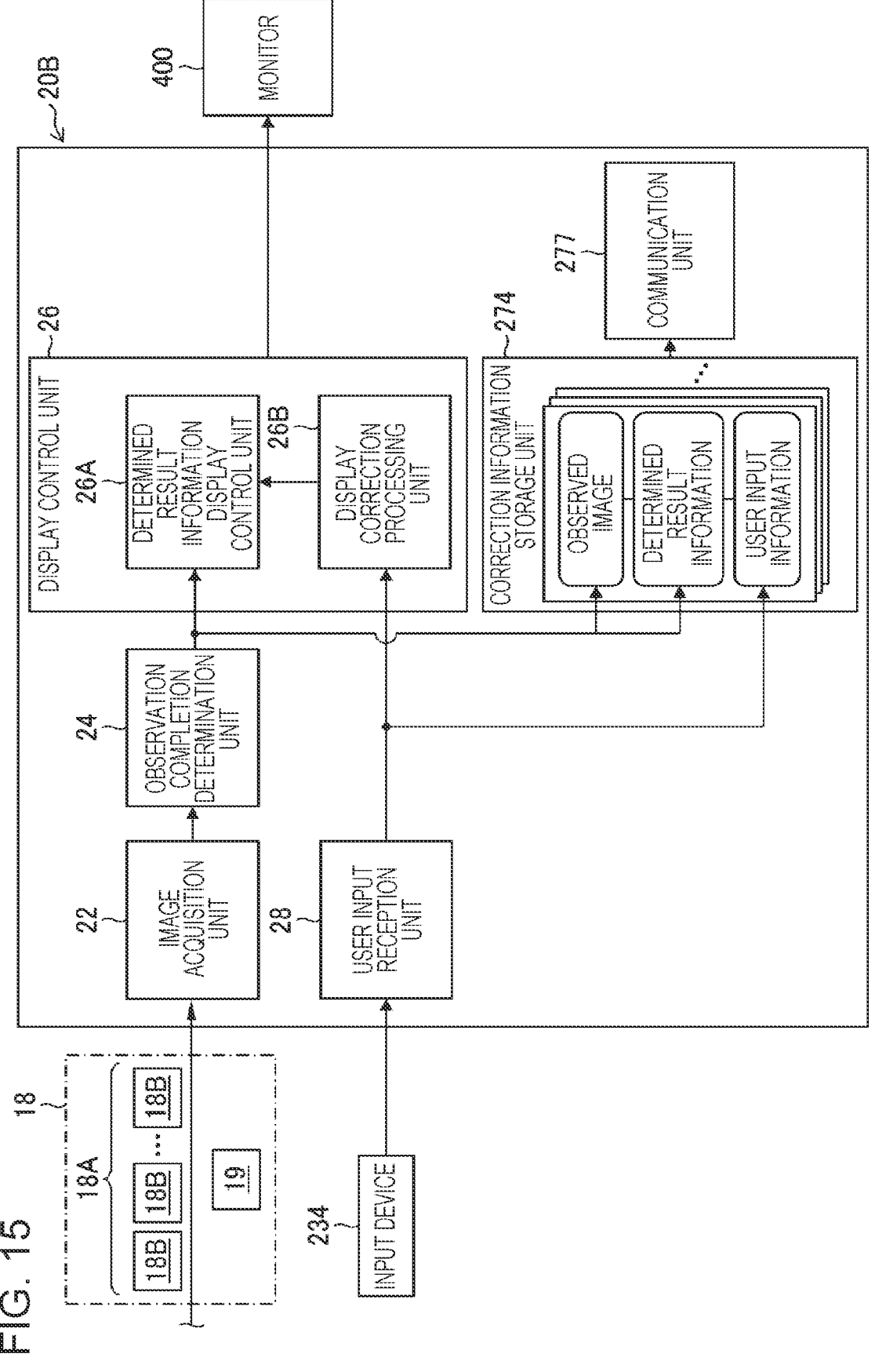
FIG. 15 is a functional block diagram illustrating functions of a medical image processing apparatus according to a second embodiment.

FIG. 15 is a functional block diagram illustrating functions of a medical image processing apparatus 20B according to a second embodiment. In FIG. 15, elements that are the same as or similar to those in the configuration illustrated in FIG. 3 are denoted by the same reference signs, and description thereof is omitted. Differences from the first embodiment will be described.

In the medical image processing apparatus 20B illustrated in FIG. 15, a function of storing determined result information by the observation completion determination program 240 and correction information by the user and a function of transmitting the stored information to an external device (not illustrated) are implemented in addition to the processing functions of the medical image processing apparatus 20 according to the first embodiment.

The medical image processing apparatus 20B includes a correction information storage unit 274 and a communication unit 277. The correction information storage unit 274 is an information storage unit that stores an observation image that is a target of the determination process performed by the observation completion determination unit 24, determined result information output by the observation completion determination unit 24 on the basis of the observation image, and user input information indicating corrected content based on the user input.

In the case where a correction instruction is input by the user via the user input reception unit 28, the medical image processing apparatus 20B associates with one another the user input information, the determined result information that is a target to be corrected based on the user input and is yet to be corrected, and the observation image from which the determined result information is obtained, that is, the observation image with which the observation completion determination unit 24 has made an erroneous determination, and stores these pieces of data in the correction information storage unit 274.

The data stored in the correction information storage unit 274 can be utilized for improving the AI model applied to the observation completion determination unit 24. For example, the observation image with which the observation completion determination unit 24 has made an erroneous determination and a label of a correct determined result input by the user for the observation image are used as learning data, and additional training of the AI model is performed. In this manner, the determination accuracy can be improved.

The data stored in the correction information storage unit 274 can be transmitted to an external device (not illustrated) via the communication unit 277. The data stored in the correction information storage unit 274 can also be stored in a portable storage medium (not illustrated) or the like and taken out to the outside of the medical image processing apparatus 20B.

The communication unit 277 communicates with the external device (not illustrated) in accordance with a predetermined communication protocol. The communication unit 277 has a configuration corresponding to the communication control unit 205 illustrated in FIG. 2 and the communication interface 227 illustrated in FIG. 14. The communication unit 277 is an example of a "communication apparatus" in the present disclosure. The external device may be, for example, a computer connected to an in-hospital network. The external device may also be a cloud server or the like installed in a facility outside the hospital. The external device may be a computer system that executes machine learning of the AI model applied to the observation completion determination unit 24, a data storage server that stores a learning dataset for machine learning, or the like.

The medical image processing apparatus 20B may transmit the correction information or the like to the external device every time the user inputs the correction instruction for the display of the determined result obtained by the observation completion determination unit 24, or may transmit a data group at a predetermined communication timing or in the case where the data group of a certain amount or more is accumulated.

Figure 16:
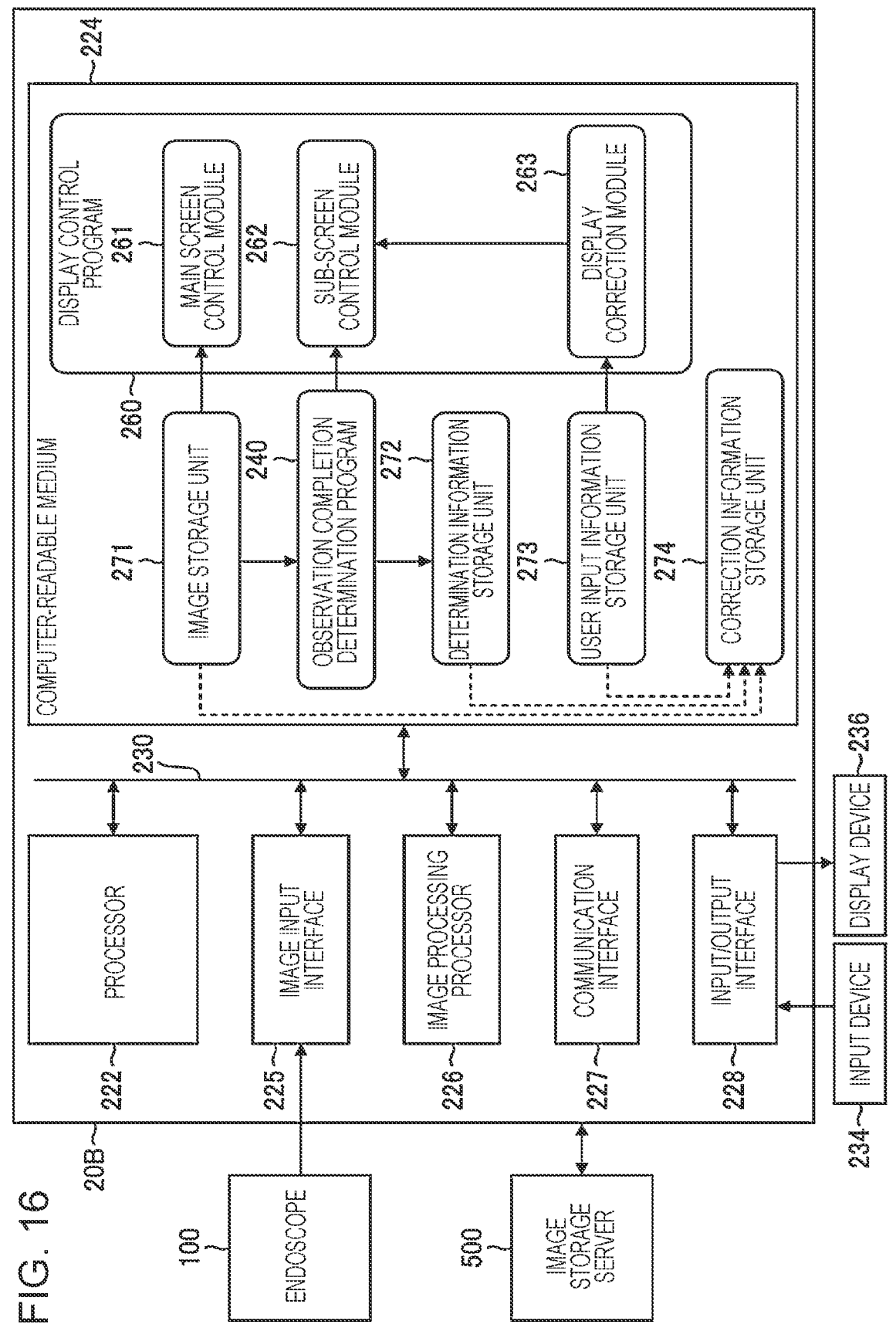
FIG. 16 is a block diagram illustrating an example of a hardware configuration of the medical image processing apparatus according to the second embodiment.

FIG. 16 is a block diagram illustrating, as an example, a hardware configuration of the medical image processing apparatus 20B according to the second embodiment. In FIG. 16, elements that are the same as or similar to those in the configuration illustrated in FIG. 14 are denoted by the same reference signs, and description thereof is omitted.

The computer-readable medium 224 of the medical image processing apparatus 20B has a storage area serving as the correction information storage unit 274. In the case where a correction instruction is input by the user for the display of the determined result of the observation completion determination obtained by the observation completion determination program 240, the processor 222 performs a process of associating an observation image from which the determined result that is a target to be corrected is obtained, the determined result information, and the user input information indicating the corrected content with one another, and storing these pieces of data in the correction information storage unit 274.

The processor 222 can transmit the data stored in the correction information storage unit 274 to an external device (not illustrated) via the communication interface 227.
Regarding Hardware Configuration of Each Processing Unit and Control Unit A hardware structure of the processing units that perform various processes such as the image processing unit 204, the communication control unit 205, and the light source control unit 350 described in FIG. 2, the image acquisition unit 22, the observation completion determination unit 24, the display control unit 26, the determined result information display control unit 26A, the display correction processing unit 26B, and the user input reception unit 28 described in FIG. 3, and the communication unit 277 described in FIG. 15 are various processors described below.

The various processors include a central processing unit (CPU) which is a general-purpose processor that executes a program to function as various processing units, a graphics processing unit (GPU) which is a processor specialized for image processing, a programmable logic device (PLD), such as a field programmable gate array (FPGA), which is a processor whose circuitry is changeable after production, a dedicated electric circuit, such as an application specific integrated circuit (ASIC), which is a processor having circuitry designed exclusively for executing specific processing, and the like.

A single processing unit may be constituted by one of these various processors, or may be constituted by two or more processors of the same kind or of different kinds. For example, one processing unit may be constituted by a plurality of FPGAs, a combination of a CPU and an FPGA, a combination of a CPU and a GPU, or the like. In addition, a plurality of processing units may be constituted by a single processor. Examples in which the plurality of processing units are constituted by a single processor include a first configuration, as exemplified by computers such as a server and a client, in which a combination of one or more CPUs and software constitutes a single processor and this processor functions as the plurality of processing units. The examples also include a second configuration, as exemplified by a System On Chip (SoC) or the like, in which a processor that implements functions of the entire system including the plurality of processing units on a single integrated circuit (IC) chip is used. As described above, the various processing units are constituted by using one or more of the various processors described above in terms of the hardware structure.

Further, the hardware structure of these various processors is, more specifically, electric circuitry in which circuit elements such as semiconductor elements are combined.
Regarding Observation Light of Endoscope System As the observation light, light in various wavelength ranges according to an observation purpose, such as white light, light in one or a plurality of specific wavelength ranges, or any combination thereof is selected. The white light is light in a white wavelength range or light in a plurality of wavelength ranges. The "specific wavelength range" is a range narrower than the white wavelength range. Specific examples of the specific wavelength range are presented below.

FIRST EXAMPLE

A first example of the specific wavelength range is, for example, a blue range or a green range in a visible range. The specific wavelength range of this first example includes a wavelength range of 390 nm or greater and 450 nm or less or a wavelength range of 530 nm or greater and 550 nm or less, and light of the first example has a peak wavelength in the wavelength range of 390 nm or greater and 450 nm or less or the wavelength range of 530 nm or greater and 550 nm or less.

SECOND EXAMPLE

A second example of the specific wavelength range is, for example, a red range in the visible range. The specific wavelength range of this second example includes a wavelength range of 585 nm or greater and 615 nm or less or a wavelength range of 610 nm or greater and 730 nm or less, and light of the second example has a peak wavelength in the wavelength range of 585 nm or greater and 615 nm or less or the wavelength range of 610 nm or greater and 730 nm or less.

THIRD EXAMPLE

A third example of the specific wavelength range includes a wavelength range in which an absorption coefficient is different between oxyhemoglobin and deoxyhemoglobin, and light of the third example has a peak wavelength in the wavelength range in which the absorption coefficient is different between oxyhemoglobin and deoxyhemoglobin. The wavelength range of this third example includes a wavelength range of 400±10 nm, a wavelength range of 440±10 nm, a wavelength range of 470±10 nm, or a wavelength range of 600 nm or greater and 750 nm or less, and light of the third example has a peak wavelength in the wavelength range of 400±10 nm, the wavelength range of 440±10 nm, the wavelength range of 470±10 nm, or the wavelength range of 600 nm or greater and 750 nm or less.

FOURTH EXAMPLE

A fourth example of the specific wavelength range is a wavelength range of excitation light that is used for observing fluorescence emitted by a fluorescent substance in a living body (fluorescence observation) and excites this fluorescent substance, and is, for example, from 390 nm to 470 nm.

FIFTH EXAMPLE

A fifth example of the specific wavelength range is a wavelength range of infrared light. The wavelength range of this fifth example includes a wavelength range of 790 nm or greater and 820 nm or less or a wavelength range of 905 nm or greater and 970 nm or less, and light of the fifth example has a peak wavelength in the wavelength range of 790 nm or greater and 820 nm or less or the wavelength range of 905 nm or greater and 970 nm or less.

Regarding Switching of Observation Light

As the type of the light source, a laser light source, a xenon light source, a light-emitting diode (LED) light source, or any combination thereof may be employed. The type of the light source, the wavelength, the presence or absence of a filter, and the like are preferably configured in accordance with the type of the photographic subject, the purpose of observation, and the like. The wavelengths of the illumination light are preferably combined and/or switched between in accordance with the type of the photographic subject, the purpose of observation, and the like at the time of observation. When the wavelengths are switched between, for example, the wavelengths of the light to be radiated may be switched between by rotating a disk-shaped filter (rotary color filter) that is disposed in front of the light source and is provided with a filter that transmits or blocks light having the specific wavelength.

The imaging element used in the electronic endoscope is not limited to a color imaging element in which a color filter is provided for each pixel, and may be a monochrome imaging element. In the case of using a monochrome imaging element, imaging can be performed in a frame sequential (color sequential) manner by sequentially switching between the wavelengths of the illumination light. For example, the wavelength of the illumination light to be emitted may be sequentially switched between violet, blue, green, and red, or the wavelength of the illumination light to be emitted may be switched by radiating wide-range light (white light) and by applying a rotary color filter (of red, green, blue, and the like) to the wide-range light. In addition, the wavelength of the illumination light to be emitted may be switched by radiating one or a plurality of narrow-range lights and by applying the rotary color filter to the one or plurality of narrow-range lights. The narrow-range lights may be infrared lights having two or more different wavelengths.

Generation Example of Special-Light Image

The processor device 200 may generate a special-light image having information in the specific wavelength range on the basis of a normal-light image obtained through imaging using white light. Note that "generation" used herein includes a concept of "acquisition". In this case, the processor device 200 functions as a special-light image acquisition unit. The processor device 200 can obtain a signal of the specific wavelength range by performing calculation based on color information of red (R), green (G), and blue (B), or color information of cyan (C), magenta (M), and yellow (Y) included in the normal-light image.

Generation Example of Feature-Quantity Image

The processor device 200 may generate, as the medical image, a feature-quantity image through calculation based on at least any of a normal-light image obtained by radiating light in the white range or light in a plurality of wavelength ranges as the light in the white range or a special-light image obtained by radiating light in the specific wavelength range. The feature-quantity image is one form of the medical image.

Illumination using Fluorescent Body

A fluorescent body may be disposed between an emission end of the light guide 170 and the illumination lenses 123A and 123B of the endoscope 100. For example, blue laser light that has passed through the light guide 170 is radiated to the fluorescent body to set the fluorescent body in an excited state, and part thereof transmits through the fluorescent body and is emitted from the illumination lenses 123A and 123B as blue light.

The fluorescent body is excited by the blue laser light to emit light (with a color of yellow) in a wide range from a wavelength region around a boundary between blue and green to a wavelength region of red in the wavelength range of light. A configuration may be employed in which this yellow light and the blue light that has transmitted through the fluorescent body may mix together to become white light, which illuminates a photographic subject through the illumination lenses 123A and 123B. Note that the blue light that has transmitted through the fluorescent body includes part of blue light emitted by the fluorescent body.

For example, the fluorescent body may have a property of emitting yellow light and transmitting blue light having a wavelength of 445 nm when being irradiated with blue laser light having the wavelength of 445 nm but transmitting most of blue laser light having a wavelength of 405 nm when being irradiated with the blue laser light having the wavelength of 405 nm. By controlling a mixing ratio of the blue laser light having the wavelength of 445 nm and the blue laser light having the wavelength of 405 nm with use of such a fluorescent body in the light source device, the ratio between the blue light that transmits through the fluorescent body and the yellow light emitted by the fluorescent body can be controlled.

First Modification

In the embodiments described above, an example in which the endoscope 100 which is a flexible endoscope is used has been described. However, the endoscope for imaging the inside of the body is not limited to the flexible endoscope, and may be a rigid endoscope or a capsule endoscope. A medical image handled by the medical image processing apparatus according to the present disclosure is not limited to an endoscopic image, and may be an image generated by another medical imaging apparatus such as an ultrasound diagnostic apparatus. The medical imaging apparatus may be, for example, at least one of an X-ray imaging apparatus, a computed tomography (CT) imaging apparatus, a magnetic resonance imaging (MRI) apparatus, or a nuclear medicine diagnostic apparatus. The technique of the present disclosure can be applied to an apparatus that processes medical images acquired using these various medical imaging apparatuses (modalities).

Second Modification

The medical image processing apparatus according to the present disclosure can be used as a diagnosis assistance apparatus that assists a doctor or the like in a consultation, a treatment, a diagnosis, or the like. The term "diagnosis assistance" includes concepts of consultation assistance, treatment assistance, examination assistance, observation assistance, and lesion identification assistance.

Third Modification

The display form for reporting whether a plurality of parts have been thoroughly observed to the user is not limited to an area display utilizing a model figure such as the schematic image 46 or a list display using text information, and may be a progress bar display indicating the progress of observation, a check list display in a format in which a check mark is attached to an observation completed part, or the like.

Application to Medical Information Management System

The medical image processing apparatus according to the present disclosure is not limited to a form in which the medical image processing apparatus is applied to the processor device 200 of the endoscope system 10 illustrated in FIG. 1, and various applications are possible. For example, the medical image processing apparatus can be applied to a medical information management system that manages various kinds of medical information including endoscopic images.

An information management apparatus in which the processing functions of the medical image processing apparatus according to the present disclosure are implemented may be installed in, for example, an operating room, an examination room, a conference room, or the like in a hospital, or may be installed in a medical institution, a research institution, or the like in a facility outside the hospital. The information management apparatus may be a workstation that assists a medical examination, a treatment, a diagnosis, or the like, or may be a work assistance apparatus that assists medical work. The work assistance apparatus may include functions of accumulating clinical information, assisting creation of diagnostic documents, assisting creation of reports, and the like.

Regarding Program for Causing Computer to Implement Functions of Medical Image Processing Apparatus A program for causing a computer to implement the functions of the medical image processing apparatus 20 or 20B described in the embodiments above may be recorded on a computer-readable medium that is a non-transitory tangible information storage medium such as an optical disc, a magnetic disk, or a semiconductor memory, and the program may be provided through this information storage medium. Instead of storing the program on such a non-transitory tangible information storage medium and providing the program, a program signal can be provided as a download service by using an electric communication line such as the Internet.

Some or all of the functions of the medical image processing apparatus described in the embodiments above can be provided as an application server, and a service of providing the processing functions may be performed via an electric communication line.

Combination of Embodiments, Modifications, etc.

The constituent elements described in the embodiments above and the constituent elements described in the modifications can be appropriately used in combination, and some of the constituent elements can be replaced.

APPENDICES

This specification includes the disclosure of the invention described below in addition to the embodiments, modifications, and the like described above.

Appendix 1

A medical image processing apparatus includes a medical image analysis processing unit and a medical image analysis result acquisition unit, in which the medical image analysis processing unit detects, on the basis of a feature quantity of pixels of a medical image, a region of interest that is a region for which attention is to be paid, and the medical image analysis result acquisition unit acquires an analysis result obtained by the medical image analysis processing unit.

The medical image analysis processing unit may include an image recognition unit.

Appendix 2

The medical image processing apparatus, in which the medical image analysis processing unit detects, on the basis of the feature quantity of the pixels of the medical image, presence or absence of a target for which attention is to be paid, and the medical image analysis result acquisition unit acquires the analysis result obtained by the medical image analysis processing unit.

Appendix 3

The medical image processing apparatus, in which the medical image analysis result acquisition unit acquires the analysis result from a recording apparatus that records the analysis result of the medical image, and the analysis result is one or both of the region of interest that is the region for which attention is to be paid and the presence or absence of the target for which attention is to be paid.

Appendix 4

The medical image processing apparatus, in which the medical image is a normal-light image obtained by radiating light in a white range or light in a plurality of wavelength ranges as the light in the white range.

Appendix 5

The medical image processing apparatus, in which the medical image is an image obtained by radiating light in a specific wavelength range, and the specific wavelength range is a range narrower than a white wavelength range.

Appendix 6

The medical image processing apparatus, in which the specific wavelength range is a blue or green range in a visible range.

Appendix 7

The medical image processing apparatus, in which the specific wavelength range includes a wavelength range of 390 nm or greater and 450 nm or less or a wavelength range of 530 nm or greater and 550 nm or less, and light in the specific wavelength range has a peak wavelength in the wavelength range of 390 nm or greater and 450 nm or less or the wavelength range of 530 nm or greater and 550 nm or less.

Appendix 8

The medical image processing apparatus, in which the specific wavelength range is a red range in a visible range.

Appendix 9

The medical image processing apparatus, in which the specific wavelength range includes a wavelength range of 585 nm or greater and 615 nm or less or a wavelength range of 610 nm or greater and 730 nm or less, and light in the specific wavelength range has a peak wavelength in the wavelength range of 585 nm or greater and 615 nm or less or the wavelength range of 610 nm or greater and 730 nm or less.

Appendix 10

The medical image processing apparatus, in which the specific wavelength range includes a wavelength range in which a light absorption coefficient is different between oxyhemoglobin and deoxyhemoglobin, and light in the specific wavelength range has a peak wavelength in the wavelength range in which the light absorption coefficient is different between oxyhemoglobin and deoxyhemoglobin.

Appendix 11

The medical image processing apparatus, in which the specific wavelength range includes a wavelength range of 400±10 nm, a wavelength range of 440±10 nm, a wavelength range of 470±10 nm, or a wavelength range of 600 nm or greater and 750 nm or less, and light in the specific wavelength range has a peak wavelength in the wavelength range of 400±10 nm, the wavelength range of 440±10 nm, the wavelength range of 470±10 nm, or the wavelength range of 600 nm or greater and 750 nm or less.

Appendix 12

The medical image processing apparatus, in which the medical image is an inside-of-living-body image of inside of a living body, and the inside-of-living-body image has information on fluorescence emitted by a fluorescent substance in the living body.

Appendix 13

The medical image processing apparatus, in which the fluorescence is obtained by irradiating the inside of the living body with excitation light whose peak wavelength is 390 nm or greater and 470 nm or less.

Appendix 14

The medical image processing apparatus, in which the medical image is an inside-of-living-body image of inside of a living body, and the specific wavelength range is a wavelength range of infrared light.

Appendix 15

The medical image processing apparatus, in which the specific wavelength range includes a wavelength range of 790 nm or greater and 820 nm or less or a wavelength range of 905 nm or greater and 970 nm or less, and light in the specific wavelength range has a peak wavelength in the wavelength range of 790 nm or greater and 820 nm or less or the wavelength range of 905 nm or greater and 970 nm or less.

Appendix 16

The medical image processing apparatus, in which a medical image acquisition unit includes a special-light image acquisition unit that acquires a special-light image having information in the specific wavelength range, on the basis of the normal-light image obtained by radiating the light in the white range or the light in the plurality of wavelength ranges as the light in the white range.

Appendix 17

The medical image processing apparatus, in which a signal of the specific wavelength range is obtained through calculation based on color information of RGB or CMY included in the normal-light image.

Appendix 18

The medical image processing apparatus including a feature-quantity image generation unit that generates a feature-quantity image through calculation based on at least one of the normal-light image or the special-light image, the normal-light image being an image obtained by radiating the light in the white range or the light in the plurality of wavelength ranges as the light in white range, the special-light image being an image obtained by radiating the light in the specific wavelength range, in which the medical image is the feature-quantity image.

Appendix 19

An endoscope apparatus including the medical image processing apparatus according to any one of appendices 1 to 18, and an endoscope that radiates at least one of light in a white wavelength range or light in a specific wavelength range and acquires an image.

Appendix 20

A diagnosis assistance apparatus including the medical image processing apparatus according to any one of appendices 1 to 18.

Appendix 21

A medical work assistance apparatus including the medical image processing apparatus according to any one of appendices 1 to 18.

Others

In the embodiments of the present invention described above, the constituent elements can be appropriately changed, added, or deleted within a scope not departing from the gist of the present invention. The present invention is not limited to the embodiments described above, and various modifications can be made by a person having ordinary skill in the equivalent related art within the technical sprit of the present invention.

REFERENCE SIGNS LIST 10 endoscope system
18 endoscopic image
18A moving image
18B frame image
20 still image
20, 20B medical image processing apparatus
22 image acquisition unit
24 observation completion determination unit
26 display control unit
26A determined result information display control unit
26B display correction processing unit
28 user input reception unit
40 screen
42 main screen
44 sub-screen
44A first sub-screen
44B second sub-screen
46 schematic image
47 observation completed part
48 observation incomplete part
51, 52, 53, 54 region block
70 hole
100 endoscope
102 handheld operation section
104 insertion section
106 universal cable
108 light guide connector
112 soft part
114 bending part
116 tip rigid part
116A tip-side end face
123 illumination unit
123A, 123B illumination lens
126 forceps port
130 imaging unit 132 imaging lens
134 imaging element
136 driving circuit
138 analog front end
140 angle knob
141 air/water supply button
142 suction button
143 function button
144 image-capturing button
170 light guide
200 processor device
202 image input controller
204 image processing unit
205 communication control unit
206 video output unit
207 storage unit
208 operation unit
209 audio processing unit
209A speaker
210 CPU
211 ROM
212 RAM
222 processor
224 computer-readable medium
225 image input interface
226 image processing processor
227 communication interface
228 input/output interface
230 bus
234 input device
236 display device
240 observation completion determination program
260 display control program
261 main screen control module
262 sub-screen control module
263 display correction module
271 image storage unit
272 determination information storage unit
273 user input information storage unit
274 correction information storage unit
277 communication unit
300 light source device
310 light source
310B blue light source
310G green light source
310R red light source
330 diaphragm
340 condenser lens
350 light source control unit
400 monitor
S12 to S20 steps of process performed by medical image processing apparatus

What is claimed is:

1. A medical image processing apparatus comprising:
at least one processor configured to
acquire a medical image,
make, on the basis of image processing including processing of recognizing a target part from the medical image, an observation completion determination as to whether observation is completed for the target part,
perform display control for causing a determined result of the observation completion determination to be displayed on a display device,
receive a user input including an instruction for correcting display content indicating the determined result of the observation completion determination, and cause corrected content based on the user input to be reflected in the display,
wherein the at least one processor is configured to make the observation completion determination by using a trained model that is trained through machine learning.

2. The medical image processing apparatus according to claim 1, further comprising:
the display device configured to display the determined result of the observation completion determination.

3. The medical image processing apparatus according to claim 1, wherein
the at least one processor is configured to
recognize an anatomic landmark for a specific part by the image processing; and
determine that the observation is completed for the specific part in a case where the anatomic landmark for the specific part is present in the medical image.

4. The medical image processing apparatus according to claim 1, wherein
the at least one processor is configured to
recognize an anatomic landmark for a specific part by the image processing; and
determine that the observation is completed for the specific part in a case where the anatomic landmark for the specific part is present in a central portion of the medical image.

5. The medical image processing apparatus according to claim 1, further comprising:
a memory, wherein
the memory is configured to store the medical image and determined result information indicating the determined result of the observation completion determination, and
in a case where the at least one processor receives the user input,
user input information, the determined result information that is a target to be corrected based on the user input and is yet to be corrected, and the medical image from which the determined result information is obtained are stored in the memory in association with one another.

6. The medical image processing apparatus according to claim 1, further comprising:
a memory; and
a communication apparatus, wherein
the memory is configured to store the medical image and determined result information indicating the determined result of the observation completion determination, and
the communication apparatus is configured to, in a case where the at least one processor receives the user input, transmit user input information, the determined result information that is a target to be corrected based on the user input and is yet to be corrected, and the medical image from which the determined result information is obtained, to an external device.

7. The medical image processing apparatus according to claim 1, wherein
the at least one processor is configured to
cause the medical image to be displayed in a first display region of the display device, and
cause the determined result of the observation completion determination to be displayed in a second display region of the display device, the second display region being different from the first display region.

8. The medical image processing apparatus according to claim 1, wherein the at least one processor is configured to cause part information on an observation completed part to be displayed using a model figure that schematically represents a part of a human body including the target part.

9. The medical image processing apparatus according to claim 1, wherein the at least one processor is configured to cause part information on an observation completed part to be displayed as text information.

10. The medical image processing apparatus according to claim 1, further comprising:

an input device to be used by a user to input the instruction, wherein the at least one processor is configured to receive the user input from the input device.

11. The medical image processing apparatus according to claim 10, wherein the input device includes at least one of a keyboard, a touch panel, a voice input device, a switch provided in an endoscope, or a foot switch.

12. The medical image processing apparatus according to claim 1, wherein the at least one processor is configured to acquire the medical images that are in time series.

13. The medical image processing apparatus according to claim 1, wherein the medical image is an endoscopic image captured using an endoscope.

14. The medical image processing apparatus according to claim 1, wherein the medical image includes an endoscope image including a plurality of frame images acquired in time series by an endoscope; and the at least one processor is configured to perform a process of the observation completion determination, for each frame image of some or all of the plurality of frame images.

15. A medical image processing apparatus comprising:

at least one processor configured to acquire a medical image, make, on the basis of image processing of the medical image, an observation completion determination as to whether observation is completed for a target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to determine that the observation is completed for a specific part in a case where the specific part is present in the medical image for a predetermined period or longer.

16. A medical image processing apparatus comprising:

at least one processor configured to acquire a medical image, make, on the basis of image processing including processing of recognizing a target part from the medical image, an observation completion determination as to whether observation is completed for the target part, perform display control for causing a determined result of the observation completion determination to be displayed on a display device, receive a user input including an instruction for correcting display content indicating the determined result of the observation completion determination, and cause corrected content based on the user input to be reflected in the display, wherein when a first condition is that an anatomic landmark for a specific part is present in the medical image, a second condition is that the specific part is present in the medical image for a predetermined period or longer, and a third condition is that the anatomic landmark for the specific part is present in a central portion of the medical image, the at least one processor is configured to recognize the anatomic landmark for the specific part by the image processing; and determine that the observation is completed for the specific part in a case where at least one condition of the first condition, the second condition, or the third condition is met.

17. A medical image processing apparatus comprising:

at least one processor configured to acquire a medical image, make, on the basis of image processing including processing of recognizing a target part from the medical image, an observation completion determination as to whether observation is completed for the target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to receive an input of an image-capturing instruction signal indicating an image-capturing timing of a still image, and determine, in a case of receiving an input of the image-capturing instruction signal, that the observation is completed for a part of which the still image is captured.

18. A medical image processing apparatus comprising:

at least one processor configured to acquire a medical image, make, on the basis of image processing including processing of recognizing a target part from the medical image, an observation completion determination as to whether observation is completed for the target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to receive the user input for correcting an observation incomplete display for a part for which the determined result of the observation completion determination indicates that the observation is incomplete, to an observation completed display indicating that the observation is completed, and change, on the basis of the user input, display content of the observation incomplete display to display content of the observation completed display.

19. A medical image processing apparatus comprising:

at least one processor configured to acquire a medical image, make, on the basis of image processing including processing of recognizing a target part from the medical image, an observation completion determination as to whether observation is completed for the target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to receive the user input for correcting an observation completed display for a part for which the determined result of the observation completion determination indicates that the observation is completed, to an observation incomplete display indicating that the observation is incomplete, and change, on the basis of the user input, display content of the observation completed display to display content of the observation incomplete display.

20. A medical image processing apparatus comprising:

at least one processor configured to acquire a medical image, make, on the basis of image processing including processing of recognizing a target part from the medical image, an observation completion determination as to whether observation is completed for the target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to receive the user input for correcting a display of part information on an observation completed part for which it is determined that the observation is completed in the observation completion determination, to a display of part information indicating another part, and correct, on the basis of the user input, display content of the part information on the observation completed part.

21. A medical image processing apparatus comprising:

at least one processor configured to acquire a medical image, make, on the basis of image processing of the medical image, an observation completion determination as to whether observation is completed for a target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to cause part information on an observation completed part to be displayed using a model figure that schematically represents a part of a human body including the target part, and cause an observation completed part and an observation incomplete part to be displayed in different colors in the model figure.

22. A medical image processing apparatus comprising:

at least one processor configured to acquire a medical image, make, on the basis of image processing of the medical image, an observation completion determination as to whether observation is completed for a target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to set a plurality of parts that are observation targets, make the observation completion determination for each part of the plurality of parts, and cause, on the basis of determined results of the observation completion determinations, information indicating an observation completed part among the plurality of parts and information indicating an observation incomplete part among the plurality of parts to be displayed.

23. A medical image processing apparatus comprising:

at least one processor configured to acquire a medical image, make, on the basis of image processing including processing of recognizing a target part from the medical image, an observation completion determination as to whether observation is completed for the target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to make the observation completion determination by using a neural network.

24. An endoscope system comprising:

an endoscope; and at least one processor, wherein the at least one processor is configured to acquire an endoscopic image obtained by imaging inside of a body by using the endoscope, make, on the basis of image processing including processing of recognizing a target part from the endoscopic image, an observation completion determination as to whether observation is completed for the target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to make the observation completion determination by using a trained model that is trained through machine learning.

25. A diagnosis assistance method implemented by at least one processor, comprising:

with the at least one processor, acquiring a medical image;

making, on the basis of image processing including processing of recognizing a target part from the medical image, an observation completion determination as to whether observation is completed for the target part;

performing display control for causing a determined result of the observation completion determination to be displayed on a display device;

receiving a user input including an instruction for correcting display content indicating the determined result of the observation completion determination; and causing corrected content based on the user input to be reflected in the display, wherein the at least one processor is configured to make the observation completion determination by using a trained model that is trained through machine learning.

26. A non-transitory, computer-readable tangible recording medium which records thereon a computer instruction which causes, when read by a computer, the computer to execute the diagnosis assistance method according to claim 25.

27. A medical image processing apparatus comprising:

at least one processor configured to acquire a medical image, make, on the basis of image processing of the medical image, an observation completion determination as to whether observation is completed for a target part, perform display control for causing a determined result of the observation completion determination to be displayed on a display device, receive a user input including an instruction for correcting display content indicating the determined result of the observation completion determination, and cause corrected content based on the user input to be reflected in the display, wherein the at least one processor is configured to perform the observation completion determination by using a trained model trained through machine learning to perform a part recognition task and an observation completion determination task.

* * * * *